US007846736B2

(12) United States Patent
Muhle et al.

(10) Patent No.: US 7,846,736 B2
(45) Date of Patent: Dec. 7, 2010

(54) METHOD FOR POLYMERIZATION REACTION MONITORING WITH DETERMINATION OF ENTROPY OF MONITORED DATA

(75) Inventors: Michael E. Muhle, Kingwood, TX (US); Ke Nguyen, Knoxville, TN (US); Charles E. A. Finney, Knoxville, TN (US); C. Stuart Daw, Knoxville, TN (US)

(73) Assignee: Univation Technologies, LLC, Houston, TX (US)

( * ) Notice: Subject to any disclaimer, the term of this patent is extended or adjusted under 35 U.S.C. 154(b) by 840 days.

(21) Appl. No.: 11/731,853

(22) Filed: Mar. 30, 2007

(65) Prior Publication Data
US 2007/0244271 A1  Oct. 18, 2007

Related U.S. Application Data

(63) Continuation-in-part of application No. 10/298,311, filed on Nov. 18, 2002, now Pat. No. 7,226,789.

(60) Provisional application No. 60/341,393, filed on Dec. 17, 2001.

(51) Int. Cl.
*G01N 31/10* (2006.01)
(52) U.S. Cl. .............................. 436/37; 436/50; 436/55; 436/86; 436/181
(58) Field of Classification Search .................. 422/62, 422/105, 108–112, 129, 130–132, 139, 147; 436/37, 50, 55, 85, 139, 142, 147–149, 155, 436/159, 181
See application file for complete search history.

(56) References Cited

U.S. PATENT DOCUMENTS 4,302,566 A    11/1981   Karol et al.
4,336,227 A *   6/1982   Koyama et al. ............. 422/111

(Continued)

FOREIGN PATENT DOCUMENTS

EP        0 233 787 B1       8/1990

(Continued)

OTHER PUBLICATIONS

Lau, I. T. et al, Fuel Processing Technology 1981, 4, 101-115.*

(Continued)

*Primary Examiner*—Arlen Soderquist

(57) ABSTRACT

In some embodiments, a method of monitoring a resin-producing polymerization reaction in a fluid bed reactor system to generate reaction parameter data in on-line fashion, determining an indicator of at least one of entropy and complexity (for example, Kolmogorov or Shannon entropy) of each of at least two subsets of the reaction parameter data, and optionally also determining from at least one value of the indicator (for example, from a time series of Kolmogorov or Shannon entropy values) an indication of at least one of degree of resin stickiness, an approach to or imminence of resin stickiness, and an approach to or imminence of an unsafe or undesired reactor operating condition (e.g., that can result in sheeting or chunking). Optionally also, the reaction is controlled in response to at least one value of the indicator, for example, in an effort to prevent the occurrence of sheeting or another discontinuity event or to maintain the reactor in a stable, non-sticking condition.

52 Claims, 5 Drawing Sheets

U.S. PATENT DOCUMENTS

| | | | | |
|---|---|---|---|---|
| 4,532,311 | A | 7/1985 | Fulks et al. | 526/62 |
| 4,803,251 | A | 2/1989 | Goode et al. | 526/59 |
| 4,858,144 | A * | 8/1989 | Marsaly et al. | 700/266 |
| 4,993,264 | A * | 2/1991 | Cody et al. | 73/579 |
| 5,022,268 | A * | 6/1991 | Wolf et al. | 73/602 |
| 5,148,405 | A | 9/1992 | Belchamber et al. | |
| 5,352,749 | A | 10/1994 | DeChellis et al. | 526/68 |
| 5,402,334 | A * | 3/1995 | Pecora et al. | 700/38 |
| 5,405,922 | A | 4/1995 | DeChellis et al. | 526/68 |
| 5,432,697 | A * | 7/1995 | Hayes | 700/38 |
| 5,435,972 | A * | 7/1995 | Daw et al. | 422/108 |
| 5,436,304 | A | 7/1995 | Griffin et al. | 526/68 |
| 5,465,219 | A * | 11/1995 | Jeffers | 700/274 |
| 5,648,581 | A | 7/1997 | Kubo et al. | 585/501 |
| 5,740,291 | A * | 4/1998 | De Lasa et al. | 385/31 |
| 5,921,679 | A * | 7/1999 | Muzzio et al. | 366/348 |
| 6,008,662 | A | 12/1999 | Newton et al. | 324/724 |
| 6,111,034 | A * | 8/2000 | Goode et al. | 526/59 |
| 6,122,557 | A | 9/2000 | Harrell et al. | 700/45 |
| 6,144,897 | A | 11/2000 | Selliers | 700/269 |
| 6,195,010 | B1 | 2/2001 | Zaldivar et al. | 340/588 |
| 6,226,549 | B1 * | 5/2001 | Deco et al. | 600/518 |
| 6,263,355 | B1 | 7/2001 | Harrell et al. | |
| 6,384,157 | B1 * | 5/2002 | Cai et al. | 526/88 |
| 6,493,691 | B1 * | 12/2002 | Neuneier et al. | 706/45 |
| 6,548,610 | B2 * | 4/2003 | Bartilucci et al. | 526/74 |
| 6,831,140 | B2 * | 12/2004 | Muhle et al. | 526/74 |
| 7,226,789 | B2 * | 6/2007 | Muhle et al. | 436/55 |
| 2002/0176455 | A1 * | 11/2002 | Triandaf et al. | 372/21 |
| 2003/0121330 | A1 | 7/2003 | Muhle et al. | 73/600 |
| 2004/0225201 | A1 * | 11/2004 | McNair | 600/300 |
| 2004/0226620 | A1 * | 11/2004 | Therriault et al. | 137/825 |
| 2005/0148742 | A1 | 7/2005 | Hagerty et al. | 526/68 |

FOREIGN PATENT DOCUMENTS

| | | |
|---|---|---|
| EP | 0 399 796 B1 | 3/1994 |
| EP | 0 385 788 B1 | 12/1994 |
| WO | 01/09196 A1 | 2/2001 |
| WO | 03/051929 A1 | 6/2003 |
| WO | 2005/113615 A2 | 12/2005 |

OTHER PUBLICATIONS

Jang, S.-S. et al, AIChE Journal 1987, 33, 26-35.*
Gyure, D. C. et al, Industrial & Engineering Chemistry Research 1987, 26, 938-944.*
Van de Velde, E. F. et al, Proceedings of the Royal Society of London, Series A: Mathematical, Physical and Engineering Sciences 1991, 434, 341-367.*
van den Bleek, C. M. et al, Chemical Engineering Journal 1993, 53, 75-87.*
Kage, H. et al, AIChE Symposium Series 1993, 296, 184-190.*
Karamavruc, A. I, et al, Powder Technology 1995, 84, 247-257.*
Hay, J. M. et al, Chemical Engineering Science 1995, 373-380.*
Elnashaie, S. S. E. H. et al, Chaos, Solitons & Fractals 1995, 5, 797-831.*
Cassanello, M. et al, Industrial & Engineering Chemistry Research 1995, 34, 2971-2980.*
Hyanek, I. et al, Industrial & Engineering Chemistry Research 1995, 34, 3872-3877.*
Elnashaie, S. S. E. H. et al, Chaos, Solitons & Fractals 1996, 7, 1317-1331.*
Elnashaie, S. S. E. H. et al, Chaos, Solitons & Fractals 1996, 7, 1955-1967.*
Schouten, J. C. et al, Chemical Engineering Science 1996, 51, 1991-2000.*
Karamavruc, A. I, et al, Powder Technology 1997, 90, 235-244.*
Christofides, P. D. et al, Journal of Process Control 1997, 7, 313-328.*
Bodruzzaman, M. et al, DE-FG22-94MT94015, 1997, 13 pages.*
Bakker, R. et al, Fractals 1997, 5, 523-530.*
Bai, D. et al, AIChE Journal 1997, 43, 1357-1361.*
Marzocchella, A. et al, AIChE Journal 1997, 43, 1458-1468.*
Ohman, M. et al, Energy & Fuels 1998, 12, 90-94.*
Alvarez, A. et al, Dynamics and Control 1998, 123-144.*
Kurtz, M. J. et al, Computers & Chemical Engineering 1998, 22, 1441-1459.*
Christofides, P. D., Industrial & Engineering Chemistry Research 1998, 37, 1893-1909.*
Ali, E. M. et al, Industrial & Engineering Chemistry Research 1998, 37, 3414-3423.*
Briens, C. L. et al, Powder Technology 1999, 102, 95-103.*
Grace, J. R. et al, Canadian Journal of Chemical Engineering 1999, 77, 305-311.*
Bai, D. et al, Industrial & Engineering Chemistry Research 1999, 38, 803-811.*
Kaart, S. et al, Catalysis Today 1999, 48, 185-194.*
Wu, W., Industrial & Engineering Chemistry Research 1999, 38, 1420-1431.*
Strozzi, F. et al, AIChE Journal 1999, 45, 2429-2443.*
Kim, S. H. et al, Korean Journal of Chemical Engineering 1999, 16, 677-683.*
Kang, Y. et al, Korean Journal of Chemical Engineering 1999, 16, 784-788.*
Cody, G. D. et al, Powder Technology 2000, 110, 128-142.*
Tsujimoto, H. et al, Powder Technology 2000, 113, 88-96.*
Ghasem, N. M., Chemical Engineering & Technology 2000, 23, 133-140.*
Gundala, R. et al, Industrial & Engineering Chemistry Research 2000, 39, 1554-1564.*
McLain, R. B. et al, Industrial & Engineering Chemistry Research 2000, 39, 3007-3017.*
Ghasem, N. M., Chemical Engineering & Technology 2001, 24, 297-303.*
Woo, K. J. et al, Chemical Engineering & Technology 2001, 24, 829-834.*
Zhao, G.-B. et al, AIChE Journal 2001, 47, 1524-1532.*
Blasetti, A. et al, Industrial & Engineering Chemistry Research 2001, 40, 4623-4632.*
Hussain, M. A. et al, Industrial & Engineering Chemistry Research 2001, 40, 5604-5620.*
Pence, D. V. et al, Chaos 1998, 8, 514-519.*
Finney, et al., "Measuring Slugging Bed Dynamics with Acoustic Sensors," *KONA: Powder and Particle* (1997) pp. 1-11.
Termonia, "Kolmogorov Entropy from a Time Series," *The American Physical Society: Rapid Communications, Physical Review A* (1984), pp. 1612-1614.
Schuster, "Deterministic Chaos: An Introduction," *Physik-Verlag GmbH* (1984), pp. 98-103 & 187-190.
Tang et al., "Data Compression and Information Retrieval via Symbolization," (1998), *Chaos 8*, pp. 688-696.
Finney et al., "Symbolic Time-Series Analysis of Engine Combustion Measurements," (1998), *SAE Technical Paper Series*: Paper No. 980624.
Schouten et al., "Maximum-likelihood Estimation of the Entropy of an Attractor," (1994), *Physical Review E 49*, pp. 126-129.
Schouten, et al., "Monitoring the Quality of Fluidization Using the Short-Term Predictability of Pressure Fluctuations," (1998), *AIChE Journal*, vol. 44, No. 1, pp. 48-60.

* cited by examiner

Fig. 1 - Fluidized Bed Reaction System

Fig. 5

[Figure: Plot of Modified Shannon entropy vs Time [5 sec timesteps], ranging from 0 to 6000 on x-axis and 0.65 to 1 on y-axis. "Unstable" is labeled near the start, and an arrow points to "Sheeting" near timestep ~5000.]

METHOD FOR POLYMERIZATION REACTION MONITORING WITH DETERMINATION OF ENTROPY OF MONITORED DATA

CROSS-REFERENCE TO RELATED APPLICATION

The application is a continuation-in-part of application Ser. No. 10/298,311, filed Nov. 18, 2002, now U.S. Pat. No. 7,226,789, which claims the benefit of U.S. Provisional Application No. 60/341,393, filed on Dec. 17, 2001, the disclosures of which are incorporated by reference in their entireties.

FIELD OF THE INVENTION

The invention pertains to methods for monitoring at least one parameter of a resin-producing polymerization reaction (e.g., an olefin polymerization reaction) in a fluidized-bed reactor and processing the resulting data in on-line fashion to generate processed data indicative of approach to or degree or imminence of resin stickiness, or resin sticking temperature, or likelihood of an unsafe reactor operating condition (e.g., one that can result in sheeting and/or chunking). Optionally also, the reaction is controlled in response to the processed data (e.g., to prevent occurrence of a reactor discontinuity event or resin stickiness).

BACKGROUND OF THE INVENTION

The expression "on-line generation" of data during a reaction is used herein to denote generation of the data sufficiently rapidly that the data is available essentially instantaneously for use during the reaction. The expression "generation of data in on-line fashion" during a reaction is used synonymously with the expression on-line generation of data during a reaction. Generation of data from a laboratory test (on at least one substance employed or generated in the reaction) is not considered "on-line generation" of data during the reaction, if the laboratory test consumes so much time that parameters of the reaction may change significantly during the test. It is contemplated that on-line generation of data can include the use of a previously generated database that may have been generated in any of a variety of ways including time-consuming laboratory tests.

With reference to a product being produced by a continuous reaction, the expression "instantaneous" value of a property of the product herein denotes the value of the property of the most recently produced quantity of the product. The most recently produced quantity typically undergoes mixing with previously produced quantities of the product before a mixture of the recently and previously produced product exits the reactor. In contrast, with reference to a product being produced by a continuous reaction, "average" (or "bed average") value (at a time "T") of a property herein denotes the value of the property of the product that exits the reactor at time T.

Throughout this disclosure, the expression "diluent" (or "condensable diluent" or "condensable diluent gas") denotes condensable gas (or a mixture of condensable gases) present in a polymerization reactor with polymer resin being produced. The diluent is condensable at the temperatures encountered in the process heat exchanger. Examples of diluents include induced condensing agents (ICAs), comonomers, isomers of comonomers, and combinations thereof.

The expression "dry polymer resin" (or "dry version" of polymer resin) is used herein to denote polymer resin that does not contain substantial amounts of dissolved gas. An example of dry polymer resin is polymer that had been previously produced in a polymerization reactor and then purged to eliminate all (or substantially all) unreacted comonomers and ICAs that had been dissolved in the polymer at the time of production. As will be discussed herein, a dry version of polymer resin has significantly different melting behavior than would the same polymer resin if it were in the presence of a significant amount of condensable diluent gas and comonomer.

The expression polyethylene denotes a polymer of ethylene and optionally one or more C3-C10 α-olefins while the expression polyolefin denotes a polymer of one or more C2-C10 α-olefins.

Throughout this disclosure, the abbreviation "MI" denotes melt index.

One commonly used method for producing polymers is gas phase polymerization. A conventional gas phase fluidized bed reactor, during operation to produce polyolefins by polymerization, contains a fluidized dense-phase bed including a mixture of reaction gas, polymer (resin) particles, catalyst, and (optionally) catalyst modifiers. Typically, any of several process control variables can be controlled to cause the reaction product to have desired characteristics.

Generally in a gas-phase fluidized bed process for producing polymers from monomers, a gaseous stream containing one or more monomers is continuously passed through a fluidized bed under reactive conditions in the presence of a catalyst. This gaseous stream is withdrawn from the fluidized bed and recycled back into the reactor. Simultaneously, polymer product is withdrawn from the reactor and new monomer is added to replace the polymerized monomer. The recycled gas stream is heated in the reactor by the heat of polymerization. This heat is removed in another part of the cycle by a cooling system external to the reactor.

It is important to remove heat generated by the reaction in order to maintain the temperature of the resin and gaseous stream inside the reactor at a temperature below the polymer melting point and/or catalyst deactivation temperature. Further, heat removal is important to prevent excessive stickiness of polymer particles that if left unchecked, may result in loss of fluidization or agglomeration of the sticky particles which may lead to formation of chunks or sheets of polymer that cannot be removed as product. This phenomenon is commonly referred to as sheeting or chunking. Further, such chunks or sheets may fall onto the distributor plate causing impaired fluidization, and in many cases forcing a reactor shutdown. Prevention of such stickiness and/or sheeting has been accomplished by controlling the temperature of the fluid bed to a temperature below the fusion or sintering temperature of the polymer particles. Above this fusion or sintering temperature, empirical evidence suggests that such fusion or sintering leads to agglomeration or stickiness, which in turn can, if left unchecked, may lead to the above conditions including sheeting.

It is understood that the amount of polymer produced in a fluidized bed polymerization process is directly related to the amount of heat that can be withdrawn from the fluidized bed reaction zone since the exothermic heat generated by the reaction is directly proportional to the rate of polymer production. In steady state operation of the reaction process, the rate of heat removal from the fluidized bed must equal the rate of rate of heat generation, such that the bed temperature remains constant. Conventionally, heat has been removed from the fluidized bed by cooling the gas recycle stream in a heat exchanger external to the reactor.

A requirement of a fluidized bed process is that the velocity of the gaseous recycle stream be sufficient to maintain the reaction zone in a fluidized state. In a conventional fluidized bed polymerization process, the amount of fluid circulated to remove the heat of polymerization is greater than the amount of fluid required for support of the fluidized bed and for adequate mixing of the solids in the fluidized bed. The excess velocity provides additional gas flow to (and through) the fluid bed for additional cooling capacity and more intensive mixing of the reactor bed. However, to prevent excessive entrainment of solids in a gaseous stream withdrawn from the fluidized bed, the velocity of the gaseous stream must be regulated.

For a time, it was thought that the temperature of the gaseous stream external to the reactor, otherwise known as the recycle stream temperature, could not be decreased below the dew point of the recycle stream without causing problems of polymer agglomeration or plugging of the reactor system. The dew point of the recycle stream is that temperature at which liquid condensate first begins to form in the gaseous recycle stream. The dew point can be calculated knowing the gas composition and is thermodynamically defined using an equation of state.

A recycle stream can be cooled to a temperature below the dew point in a fluidized bed polymerization process resulting in condensing a portion of the recycle gas stream. The resulting stream containing entrained liquid is then returned to the reactor without causing agglomeration, and/or plugging phenomena. The process of purposefully condensing a portion of the recycle stream is known in the industry as "condensed mode" operation in a gas phase polymerization process.

When a recycle stream temperature is lowered to a point below its dew point in "condensed mode" operation, an increase in polymer production is possible, as compared to production in a non-condensing mode because of increased cooling capacity. Consequently, a substantial increase in space-time yield, the amount of polymer production in a given reactor volume, can be achieved by condensed mode operation with little or no change in product properties.

Cooling of the recycle stream to a temperature below the gas dew point temperature produces a two-phase gas/liquid mixture with solids contained in both of these phases. The liquid phase of this two-phase gas/liquid mixture in "condensed mode" operation remains entrained or suspended in the gas phase of the mixture. Vaporization of the liquid occurs only when heat is added or pressure is reduced. In some conventional processes, vaporization occurs when the two-phase mixture enters the fluidized bed, with the (warmer) resin providing the required heat of vaporization. The vaporization thus provides an additional means of extracting heat of reaction from the fluidized bed. The heat removal capacity is further enhanced in condensed mode operation by the lower gas temperatures of the gas stream entering the fluidized bed. Both of these factors increase the overall heat removal capability of the system and thereby enable higher space-time yields (higher reactor production rates per unit volume of the fluidized bed).

The cooling capacity of recycle gas can be increased further while at a given reaction temperature and a given temperature of the cooling heat transfer medium. One option described is to add non-polymerizing, non-reactive materials to the reactor, which are condensable at the temperatures encountered in the process heat exchanger. Such non-reactive, condensable materials are collectively known as induced condensing agents (ICAs). Increasing concentrations of ICA in the reactor causes corresponding increases in the dew point temperature of the reactor gas, which promotes higher levels of condensing for higher (heat transfer limited) production rates from the reactor. Suitable ICA materials are selected based on their specific heat and boiling point properties. In particular, an ICA compound is selected such that a relatively high portion of the material is condensed at the cooling water temperatures available in polymer production plants, which are typically 20-40° C. ICA materials include hexane, isohexane, pentane, isopentane, butane, isobutane and other hydrocarbon compounds that are similarly non-reactive in the polymerization process.

U.S. Pat. No. 5,352,749, to DeChellis et al, teaches that there are limits to the concentrations of condensable gases, whether ICA materials, comonomers or combinations thereof, that can be tolerated in the reaction system. Above certain limiting concentrations, the condensable gases can cause a sudden loss of fluidization in the reactor, and a consequent loss in ability to control the temperature in the fluid bed. The above-cited U.S. Pat. No. 5,352,749, and U.S. Pat. Nos. 5,405,922 and 5,436,304, disclose upper limits of ICA in the reactor, depending on the type of polymer being produced. U.S. Pat. No. 5,352,749 discloses that a limiting concentration of ICA (isopentane) exists, beyond which the reactor contents suddenly loose fluidization. The authors characterized this limit by tracking the ratio of fluidized bulk density to settled bulk density. As the concentration of isopentane was increased, they found that the bulk density ratio steadily decreased. When the concentration of isopentane was sufficiently high, corresponding to a bulk density ratio of 0.59, they found that fluidization in the reactor was lost. They therefore determined that this ratio (0.59) was a point of no return, below which the reactor will cease functioning due to loss of fluidization.

As described in PCT Application Publication Number WO 2005/113615(A2), attempts to operate polymerization reactors with excessive ICA concentrations cause polymer particles suspended in the fluid bed to become cohesive or "sticky," and in some cases cause the fluid bed to solidify in the form of a large chunk. This stickiness problem is characterized by undesirable changes in fluidization and mixing in the fluid bed, which if left unchecked, may develop into a reactor discontinuity event, such as sheeting in the straight sided reaction section, sheeting in the dome of such a reactor or chunking, any of which can lead to reactor shut-downs, which in large scale reactors are expensive. These solid masses (sheets or chunks) of polymer eventually become dislodged from the walls and fall into the reaction section and settle on the distributor plate, where they interfere with fluidization, block the product discharge port, and usually force a reactor shut-down for cleaning. The term "discontinuity event" is used to describe a disruption in the continuous operation of a polymerization reactor caused by sheeting, chunking or distributor plate fouling. The terms "sheeting and/or chunking" while used synonymously herein, may describe different manifestations of problems caused by excessive polymer stickiness in the fluid bed. In either manifestation (sheeting or chunking) the excessive polymer stickiness can lead directly to a reactor discontinuity event with the associated loss production.

Desirable, smooth operation of a fluidized bed polymerization reactor system is generally characterized by efficient, random mixing of particles in the fluidized bed. Undesirable operation is typically characterized by non-uniformities, including "hot spots," "cold bands" (caused by insulating layers of fines), and polymer agglomerates (e.g., chunks or sheets) in the reactor.

The parent application (published as U.S. Patent Application Publication Number US 2003/0121330 A1) and corresponding PCT Application Publication Number WO 03/051929 describe use of mathematical chaos theory to detect the onset and presence of sheeting in a fluidized bed reactor, and teaches generating time series data from the output of a range of instruments, including acoustic emission sensors, fluidized bulk density sensors, differential pressure sensors, static sensors, and wall temperature sensors, processing the data in accordance with methods of non-linear dynamics herein referred to as chaos theory and comparing the resulting processed data to data from a control reactor running without sheeting. In some embodiments disclosed therein, the onset of sheeting is indicated by an increase in mean "cycle time" associated with the time series (relative to mean cycle time in a baseline, control reaction), usually with a concurrent decrease in the "mean deviation" of the time series, or by a decrease in mathematical "entropy" (e.g., Kolmogorov entropy or Shannon entropy) of the time series data as compared to the entropy of time series data from a control reaction running without sheeting. FIG. 10 of the parent application is a plot of Kolmogorov entropy of each of a number of sub-sequences of a time series of fluidized bulk density data values (resulting from measurements during a polymerization reaction) versus time. FIG. 9 of the parent application is a plot of modified Shannon entropy of data (measured during a polymerization reaction) versus time.

It has been proposed in the literature to measure data from fluidized bed (and other) reactors in contexts other than during performance of a resin polymerization reaction in any such reactor, to generate Kolmogorov entropy (or other mathematical entropy) values from the measured data and to determine from the entropy values some characteristic of operation of the reactors. For example, Finney, et al., in the paper "Measuring Slugging Bed Dynamics with Acoustic Sensors," submitted to KONA: Powder and Particle (1997), teach determining Kolmogorov entropy of acoustic data and DP (differential pressure) data and using Kolmogorov entropy of acoustic data to predict or detect "slugging" in a fluidized bed.

However, until the present invention it had not been known how to generate reaction parameter data in on-line fashion by measuring at least one parameter of a polymerization reaction in a fluidized bed reactor, and to generate Kolmogorov entropy (or other mathematical entropy) values from the measured reaction parameter data and to use the entropy values as an indicator of the degree (or imminence) of polymer resin stickiness or of approach to unsafe polymerization reactor operating conditions leading to at least one of sheeting and chunking.

It would be desirable to provide a method of determining a stable operating condition for fluidized bed polymerization, especially if operating in condensed mode, to facilitate optimum design of the plant and determination of desirable process conditions for optimum or maximum production rates for a given plant design.

It would also be desirable to have a mechanism in commercial gas-phase polymerization reactors to detect the onset of stickiness that is a better or earlier indicator of the onset of stickiness than are conventional techniques (e.g., monitoring the fluidized bulk density as described in U.S. Pat. No. 5,352,749). Such a mechanism would allow the operators to determine when conditions of limiting stickiness are being approached, and enable them to take corrective action before discontinuity events (such as sheeting and chunking) occur, while keeping the reactors at or near conditions that permit higher production rates with substantially less risk. In a class of embodiments, the present invention provides a better indicator of onset of resin stickiness (and of degree of resin stickiness and of imminence of unsafe polymerization reactor operating conditions) than do conventional techniques, using Kolmogorov entropy or other mathematical entropy values determined from the measured polymerization reaction parameter data.

Polymerization reaction parameter data to be processed in accordance with some embodiments of the present invention are indicative of a sequence of static charge values. Such data can be generated by monitoring a polymerization reaction using one or more static probes in any of a variety of conventional ways (e.g., as described in US Patent Application Publication No. 2005/0148742, published Jul. 7, 2005). US Patent Application Publication No. 2005/0148742 describes use of static probes positioned in the entrainment zone of a fluidized bed polymerization reaction system to monitor "carryover static" during a polymer resin-producing polymerization reaction in the reactor system, and describes control of the reaction in response to the results of such monitoring to prevent discontinuity events such as chunking and sheeting (e.g., to reduce carryover static and thereby prevent such discontinuity events). The expression "entrainment zone" of a fluidized bed reactor system is used in US Patent Application Publication No. 2005/0148742 and the present disclosure to denote any location in the reactor system outside the dense phase zone of the system (i.e., outside the fluidized bed). However, US Patent Application Publication No. 2005/0148742 does not suggest wavelet transforming static charge data (or other data) or determining the kurtosis of a set of static charge data values (or other data values).

The expression "carryover static" is used in US Application Publication No. 2005/0148742 and the present disclosure to denote static charging that results from frictional contact by particles (e.g., catalyst particles and resin particles) against the metal walls of a gas recycle line, or against other metal components in a reactor entrainment zone. Carryover static can be measured by suitable static probes positioned in various sections of the entrainment zone of a reaction system, including the expanded (disengagement) section, the recycle line, and the distributor plate.

In the present disclosure, the expression "entrainment static" denotes carryover static that results from frictional contact between entrained particles and a static probe located in a gas recycle line of a fluidized bed reactor system. Thus, the term "entrainment static" represents a specific means of measuring the carryover static generated by frictional contact of entrained particles that occur throughout the gas recycle system.

SUMMARY OF THE INVENTION

In a first class of embodiments, the inventive method includes the steps of: (a) monitoring at least one reaction parameter of a polymerization reaction in a fluidized bed reactor system to generate (in on-line fashion) time-domain reaction parameter data (i.e., a time series of reaction parameter values), which may be, for example, differential or absolute pressure, acoustic emission, temperature, carryover static or bed static data values indicative of resin stickiness, or other reaction parameter data values; and (b) determining mathematical entropy (e.g., Kolmogorov entropy or Shannon entropy) of each of at least two subsets of the reaction parameter data, each of the subsets including reaction parameter data values indicative of a different time interval (window) during the reaction. Typically, the method also includes a step of determining from entropy values (e.g., Kolmogorov entropy values) generated in step (b) at least one indication of at least one of degree of resin stickiness, approach to or imminence of resin stickiness, likelihood of imminent resin stickiness, and an approach to or imminence of an unsafe or undesired reactor operating condition (e.g., an operating condition likely to lead to at least one discontinuity event).

In alternative embodiments, an indicator (e.g., an indicator other than Kolmogorov or Shannon entropy) of at least one of entropy and complexity of each of at least two subsets of the reaction parameter data is determined in step (b) In these embodiments, the method typically also includes a step of determining from values of the indicator (e.g., a signal or data indicative of entropy or complexity or an aspect of entropy or complexity) generated in step (b) at least one indication of at least one of degree of resin stickiness, approach to or imminence of resin stickiness, likelihood of imminent resin stickiness, and an approach to or imminence of an unsafe or undesired reactor operating condition. An example of such an indicator is a Lyapunov exponent (or corresponding eigenvalue) of each subset of the reaction parameter data.

Where a sequence of reaction parameter data values to be processed in accordance with the invention are described as a one-dimensional function of time (e.g., they are a sequence of data values, $x_{n+1}$, that satisfy $x_{n+1}=f(x_n)$, where each index corresponds to a time and "f" is a function), the Kolmogorov entropy of the data values is the Lyapunov (Liapunov) exponent of the data values. Where a sequence of reaction parameter data values to be processed in accordance with the invention are described as a multi-dimensional function of time, the data values have a set of at least two Lyapunov exponents (each having a corresponding eigenvalue), and the Kolmogorov entropy of the data values is a well known function of the Lyapunov exponents (typically, it is simply the sum of those Lyapunov exponents that are positive exponents). In some embodiments of the inventive method, step (b) includes determination of at least one Lyapunov exponent (or at least one eigenvalue corresponding thereto) of each of at least two subsets of the reaction parameter data.

Kolmogorov entropy, Lyapunov exponents (and corresponding eigenvalues), and Shannon entropy are well known concepts and are discussed below.

In some preferred embodiments of the inventive method, the reactor system includes a product discharge vessel (sometimes referred to as a product discharge "chamber") into which polymer product is discharged from the fluidized bed reactor, and step (a) includes the step of measuring product chamber static data indicative of static charge transferred from the polymer product to the product discharge vessel (e.g., total static charge transferred to the vessel in a selected time interval). The product chamber static data can be measured with the product chamber vessel functioning as a Faraday cup as the polymer product is discharged into it from the fluidized bed reactor. In a typical fluidized bed reactor system, the product discharge vessel has capacity to contain a large amount (e.g., 3000 lbs) of polymer product, and thus static charge indicative of a large amount of polymer product can be transferred to the product discharge vessel and measured to generate the product chamber static data during step (a). Typically, Kolmogorov entropy values generated in response to product chamber static data are reliably indicative of imminent wall sheeting. In contrast, measuring the static charge transferred (from polymer product and other substances within the reactor system) to a smaller element of the reactor system (e.g., a distributor plate or a static charge sensor in a gas recycle line) would generate static data indicative of charge of smaller amounts of polymer product, and Kolmogorov entropy values generated in response thereto would be less reliably indicative of imminent wall sheeting.

In some preferred embodiments, "high speed" reaction parameter data are generated and processed in accordance with the invention. The expression "high speed" data is used herein to denote times series data values (indicative of a sequence of measured data samples) collected with a sample rate greater (and typically much greater) than 1 Hz. For example, in some embodiments at least one high speed skin thermocouple is used to generate time-domain reaction parameter data that are processed in accordance with the invention. A high speed thermocouple is configured to sense reactor temperature excursions of shorter duration than can a conventional thermocouple. A "high speed" (or "fast") thermocouple has sufficiently fast response to be sensitive to temperature spikes of duration on the order of a second (e.g., spikes having duration of one second or a few seconds) and is typically positioned not more than one half inch from the reactor wall.

In some embodiments of the inventive method, the reaction parameter data generated in step (a) are static data other than product chamber static data. For example, the reaction parameter data may be or include one or more of bed static data indicative of static charge in the fluidized bed of a fluidized bed reactor (such static charge is sometimes referred to herein as reactor or "bed" static charge); carryover static data indicative of carryover static (e.g., entrainment static); and static charge measured using a single static sensor in an expanded section of the reactor above the fluidized bed). In other embodiments, some or all of the reaction parameter data generated in step (a) are not indicative of static charge. For example, in some embodiments, the reaction parameter data generated in step (a) are (or include) one or more of: acoustic or pressure (e.g., differential pressure) data; fluidized bulk density data from appropriate sensors; and temperature data from one or more skin temperature sensors, wall temperature sensors, and/or other temperature sensors.

Reaction monitoring in accordance with the invention can be used to identify when reaction conditions deviate from desirable operating conditions which are typically characterized by efficient, random mixing of particles in the reaction zone. Undesirable operating conditions are typically characterized by non-uniformities, including hot spots, cold bands caused by insulating layers of fines, and fused polymer sheets.

In preferred embodiments, relevant measured data from all reaction monitoring instruments, and relevant calculated values, are combined into an integrated computer display for presentation to users (e.g., plant operators). Such a computer display can be supplemented by process alarms or advisory notices to warn the users of conditions in the process that may be approaching those that will lead to sheeting (e.g., wall or dome sheeting) or another discontinuity event. The alarms or advisory notices can also be combined with recommended control actions to avoid the discontinuity event.

In some implementations of the above-mentioned embodiments, the inventive method also includes the step of controlling the reaction in response to entropy values (or other indicators of entropy or complexity) generated in step (b), typically in an effort to prevent (and preferably to prevent) the occurrence of sheeting or another discontinuity event and/or to maintain the reactor in a stable, non-sticking condition. For example, the control may be implemented by adjusting reaction temperature, or changing the superficial velocity of fluidizing gas, or controlling the feed rate of a continuity additive (e.g., aluminum distearate (sometimes referred to herein as "A" material) or ethoxylated amine (sometimes referred to herein as "B" material), either neat or in oil slurry) into the reactor.

Other aspects of the invention are systems including (and methods of using) sensors and optionally also other instruments for monitoring reaction parameters (e.g., parameters indicative of static charge, acoustic, temperature, and/or DP values, where "DP" values are pressure differences between two different locations along the length of the fluid bed), and processors programmed to process the resulting reaction parameter data in accordance with any embodiment of the inventive method (typically to generate data, or signals, or a display indicative of imminent occurrence of resin sheeting or another discontinuity event). In preferred embodiments, relevant measured data from all reaction monitoring instruments, and relevant calculated values, are combined into an integrated computer display for presentation to users (e.g., plant operators).

BRIEF DESCRIPTION OF THE DRAWINGS

FIG. 5 is a plot of Shannon entropy of subsets of a time series of temperature data values generated from the high-pass-filtered output of skin temperature sensors (e.g., skin temperature sensors 8 of FIG. 1) that monitored a polymerization reaction in a fluidized bed reactor. The entropy values are plotted versus time in units of 5 second intervals.

DETAILED DESCRIPTION OF PREFERRED EMBODIMENTS

Figure 1:
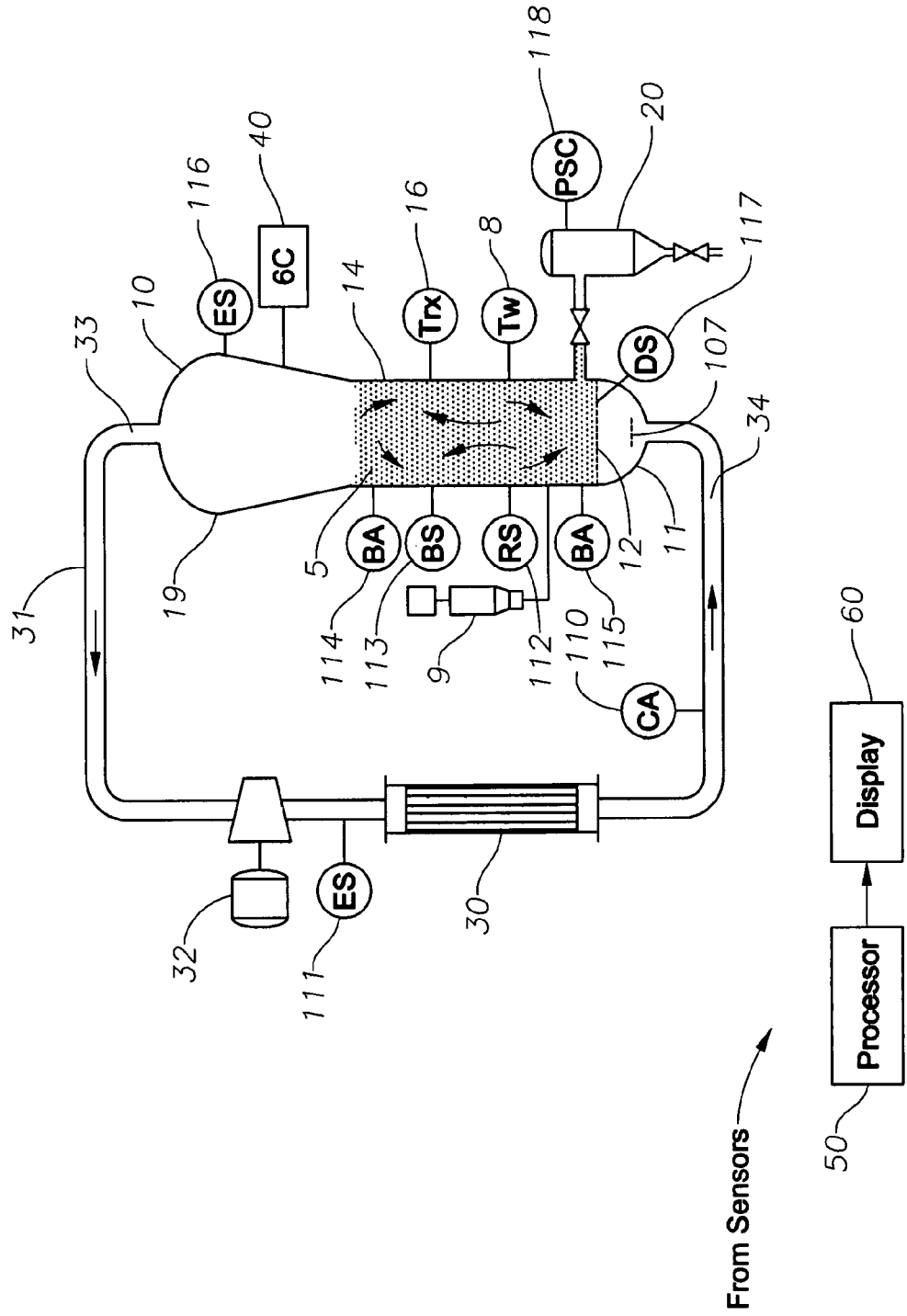
FIG. 1 is a simplified cross-sectional view of a reaction system, including fluidized bed reactor 10, whose operation can be monitored and optionally also controlled in accordance with the invention.

A reactor system whose operation can be monitored and optionally also controlled in accordance with the invention will be described with reference to FIG. 1. The FIG. 1 system includes fluidized bed reactor 10. Reactor 10 has a bottom end 11, a top expanded section 19, a cylindrical (straight) section 14 between bottom end 11, and a distributor plate assembly 12 (sometimes referred to as a distributor plate) within section 14. A fluidized bed 5 of granular polymer and catalyst particles is contained within the straight section 14. The bed is fluidized by the steady flow of recycle gas through distributor plate 12. The flow rate of fluidizing gas is regulated to provide the fluidized bed with relatively good mixing, as illustrated in the figure.

The reactor system also has a catalyst feeder 9 for controlled addition of polymerization catalyst to the fluidized bed (the reaction zone). Within the reaction zone, the catalyst particles react with the monomer (e.g., ethylene) and comonomer and optionally other reaction gas to produce granular polymer particles. As new polymer particles are produced, other polymer particles are continually withdrawn from the fluidized bed through product discharge subsystem 20 (which includes a product discharge chamber). After passing through the product discharge subsystem, the polymer granules are degassed (or "purged") with a flow of inert nitrogen to remove substantially all of the dissolved hydrocarbon materials.

The reactor system of FIG. 1 also has a cooling control loop which includes a recycle gas line 31, a circulating gas cooler 30 and compressor 32, coupled with reactor 10 as shown. During operation, the cooled circulating gas from cooler 30 flows through inlet 34 into reactor 10, then propagates upward through the bed and out from reactor 10 via outlet 33.

The expanded section 19 is also known as the "velocity reduction zone," and is designed to minimize the quantities of particle entrainment from the fluidized bed. Each diameter of each horizontal cross-section of the expanded section 19 is greater than the diameter of straight section 14. The increased diameter causes a reduction in the speed of the fluidizing gas, which allows most of the entrained particles (catalyst and resin particles) to settle back into the fluidized bed, thereby minimizing the quantities of solid particles that are "carried over" from the fluidized bed (at a given value of fluidizing gas velocity) through the recycle gas line 31.

Continuity additive feed 110 introduces a continuity additive (e.g., slurry of "B" material in mineral oil in one embodiment) into the fluid stream within line 31.

Fluidized bed reactor 10 has an annular disk flow deflector 107 at its bottom end (at reactor inlet 34, which is the outlet of recycle line 31).

One or more temperature sensors 16 are located in the fluidized bed, and are used with a control system (which can include processor 50 of FIG. 1) and an external cooling loop to control the fluidized bed temperature Trx near the process set-point. Relatively warm reactor gas (whose temperature has increased during its flow through reactor 10) is withdrawn from outlet 33 and is pumped by compressor 32 to cooler 30, wherein the temperature of the gas (the cooling fluid) is reduced. Relatively cool fluid (which may contain condensed liquid) flows out from cooler 30 to the reactor inlet 34, to cool the fluidized bed. Temperature sensors (not shown) near the inlet and outlet of cooler 30 provide feedback to the control system regulate the amount by which cooler 30 reduces the temperature of the fluid entering reactor 10. During operation, cooled circulating gas from cooler 30 flows through annular disk 107 into reactor 10, then propagates upward through the bed and out from reactor 10 into inlet 33 of recycle line 31.

Reactor 10 can be implemented as an mLLDPE (metallocene-catalyzed, linear low-density polyethylene) reactor with straight section 14 having height 47 feet, six inches.

In addition to bed temperature sensor(s) 16 noted above, the FIG. 1 system also includes other sensors for generating reaction parameter data during a polymerization reaction.

The data are processed in accordance with the invention in processor 50, typically to generate a display (60) indicative of at least one of a degree of resin stickiness, an approach to or imminence of resin stickiness, and an approach to or imminence of or an unsafe or undesired reactor operating condition (e.g., likelihood of an imminent discontinuity event). The sensors include entrainment static probe 111, distributor plate static sensor 117, upper and lower bed acoustic emission sensors 114 and 115, reactor static probes 112 and 113, one or more skin temperature sensors 8, expanded section static probe 116, product discharge chamber static sensor 118, and optionally also differential pressure sensors (not shown) configured to sense differential pressure in bed 10.

Each skin temperature sensor 8 is configured and positioned to sense the temperature $T_w$ of the resin (or other reactor contents) near the wall of reactor 10 during operation. Each skin temperature sensor 8 is typically implemented as a thermocouple sensor having fast response design and mounted along the reactor wall so as to protrude into fluidized bed 5 (and/or the volume above bed 5) from the reactor wall by a small amount (e.g., one eighth to one quarter of an inch).

Each bed temperature sensor 16 is positioned in the fluidized bed, and is used with a control system (which can include processor 50 of FIG. 1) and the external cooling loop to control the fluidized bed temperature Trx to be near to the process set-point. Each bed temperature sensor 16 can be a resistance temperature sensor positioned and configured to sense bed temperature during reactor operation at a location within reactor 10 away from the reactor wall. The resistance temperature sensor can be mounted so as to protrude into the bed (e.g., eight to eighteen inches away from the reactor wall) more deeply than does skin temperature sensor 8. In some preferred embodiments, each skin temperature sensor 8 is a high speed skin thermocouple. A high speed thermocouple can sense reactor temperature excursions of shorter duration than can a conventional thermocouple. Detection of such short duration temperature excursions can be necessary to generate reaction parameter data that are useful to perform typical embodiments of the inventive method.

In operation, entrainment static probe 111 positioned between compressor 32 and cooler 30 generates reaction parameter data by monitoring the static charge of entrained particles within line 31.

Reactor static probes 112 and 113 (and optionally also at least one other reactor static probe) are used to monitor the static charge at or near the reactor wall within fluidized bed 5. Reactor static probe 113 is located in the upper portion of fluidized bed 5 and is thus sometimes referred to herein as an "upper bed" reactor static probe (or "upper bed" static probe).

Additional static probes can also be used to monitor the static charge at other locations of the reactor system. For example, distributor plate static probe 117 can be positioned near to (e.g., on or at) distributor plate 12 to monitor the static charge at or near to distributor plate 12, and an annular disk static probe can be positioned near to (e.g., on or at) annular disk 107 to monitor the static charge at or near to disk 107.

Electrostatic activity in a reactor system can be monitored by the specific static probes described herein or other static probes to generate reaction parameter data to be processed in accordance with the invention. A static probe typically includes a metallic probe tip, one or more signal wires, an electrical feed-through, and a measuring instrument. The probe tip may comprise a cylindrical rod, but could be any cross sectional form such as square, rectangular, triangular, or oblong. In various embodiments, the probe tip is made of any of a variety of conductive materials. With respect to the signal wires, any conventional insulated wire may be used. With respect to the electrical feed-through, any suitable feed-through may be used as long as it provides the necessary electrical isolation from ground (and the reactor walls), and provides the required pressure seal to prevent leakage of high pressure reactor gases from the reactor. Electrical feed-throughs suitable for use in typical embodiments are available commercially.

In the FIG. 1 system, reactor gas composition may be measured using gas chromatograph system 40. Monitored reactor gas composition parameters can be or include concentrations (and partial pressures) of all reactant gases and induced condensing agents (ICAs), as well as all inert gases (such as nitrogen, hydrocarbon inerts, etc.) that are present in relevant quantities.

The FIG. 1 system optionally also employs other sensors and also other apparatus to measure other reaction parameters during a polymerization reaction. Such other reaction parameters can include instantaneous and bed-averaged resin product properties (e.g., melt index and density of the polymer resin product being produced by the FIG. 1 system during a polymerization reaction). Resin product properties are conventionally measured by periodically sampling the resin as it exits the reactor (e.g. once per hour), and performing the appropriate tests in a quality control laboratory.

It is well known how to control various process control variables (e.g., to control gas phase composition within reactor 10, the concentration of induced condensing agents (ICAs) and comonomer introduced into reactor 10, partial pressure of at least one reactant (e.g., ethylene) introduced into reactor, and the type and properties of each catalyst introduced into reactor 10, and to use elements 30 and 32 in the manner described above to control temperature) to control various reactions performed by the FIG. 1 system. For example, it is known how to control a polymerization reaction during a transition by controlling process control variables such that the product (granular polymer resin) has properties compliant with an initial specification set at the start of the transition, the product produced during the transition ceases to comply with the initial specification set at a first time, and the product has properties compliant with a final specification set at the end of the transition.

In typical embodiments of the invention, a reaction (e.g., a steady-state reaction and/or a reaction transition) performed by a polymerization reactor is controlled by adjusting (or regulating) controlling process variables in response to at least one control variable determined from reaction parameter data processed in accordance with the invention. Each such control variable is determined based on a processed version of data output from sensors (and optionally also other apparatus) that measure reaction parameters. Processor 50 of FIG. 1 is an example of a processor programmed to process reaction parameter data in on-line fashion in accordance with the invention and to generate one or more of such control variables in on-line fashion in accordance with any of various embodiments of the invention in response to the processed reaction parameter data (e.g., a processed version of the output of one or more of temperature sensor(s) 16, skin temperature sensor(s) 8, sensors 111, 112, 113, 114, 115, 116, 117, and 118, and gas chromatograph 40, and optionally also a processed version of resin density and/or MI or other resin properties measured during the reaction). Optionally also, processor 50 is programmed to control (or cause other elements of the FIG. 1 system to control) the reaction in response to each control variable. Processor 50 may be a separate, stand alone processor, or it may be integral with other process control computers that are conventionally used to monitor and control the reactor system.

Preferably, processor 50 is configured and programmed to process reaction parameter data from all or some of the system's reaction monitoring instruments, and optionally also to combine the resulting processed data with relevant calculated parameters into an integrated computer display for presentation to users (e.g., plant operators). An example of such a computer display is display 60 of FIG. 1. The computer display can be supplemented by process alarms or advisory notices (e.g., an "excessive static indication" notice) to users to warn of conditions in the process that may be approaching those that will lead to sheeting (e.g., wall or dome sheeting) or another discontinuity event. Such alarms or advisory notices can also be combined with recommended control actions to avoid the discontinuity event (e.g., recommended control actions displayed as part of the display 60). For example, in response to entropy values generated in accordance with the invention, an advisory could be generated with a displayed (or otherwise promulgated) recommendation to reduce the reactor temperature and/or isopentane concentration to avoid dome sheeting.

In a class of embodiments, the inventive method includes the steps of: (a) monitoring at least one reaction parameter of a polymerization reaction in a fluidized bed reactor system to generate (in on-line fashion) time-domain reaction parameter data (i.e., a time series of reaction parameter values); and (b) determining mathematical entropy (e.g., Kolmogorov entropy or Shannon entropy) of each of at least two subsets of the reaction parameter data, each of the subsets including reaction parameter data values indicative of a different time interval (window) during the reaction. Typically, the method also includes a step of determining from entropy values (e.g., Kolmogorov entropy values) generated in step (b) at least one indication of at least one of degree of resin stickiness, approach to or imminence of resin stickiness, likelihood of imminent resin stickiness, and an approach to or imminence of an unsafe or undesired reactor operating condition.

In alternative embodiments, an indicator (other than Kolmogorov or Shannon entropy) of entropy or complexity of each of at least two subsets of the reaction parameter data is determined in step (b). In these embodiments, the method typically also includes a step of determining from the indicator (e.g., a signal or data indicative of entropy or complexity or an aspect of entropy or complexity) generated in step (b) at least one indication of at least one of degree of resin stickiness, approach to or imminence of resin stickiness, likelihood of imminent resin stickiness, and an approach to or imminence of an unsafe or undesired reactor operating condition. An example of such an indicator is a Lyapunov exponent (or corresponding eigenvalue) of each subset of the reaction parameter data.

Kolmogorov entropy, Lyapunov exponents (and corresponding eigenvalues), and Shannon entropy are well known concepts and are discussed, for example, in above-cited U.S. Patent Application Publication No. US 2003/0121330 and the references cited therein, and in Termonia, "Kolmogorov Entropy from a Time Series," Physical Review A, March 1984, pp 1612-1614, and Schuster, "Deterministic Chaos: An Introduction," Physik-Verlag GmbH (1984), pp 98-103 and 187-190. It is well known how to determine these quantities from time series data values. It is also well known how to program processors to determine Kolmogorov entropy, Lyapunov exponents, and Shannon entropy of a set of time series data values efficiently. Commercially available software (e.g., the MATLAB software available from Math-Works, Inc.) can be used to program processors to determine Kolmogorov entropy and Shannon entropy of a set of time series data values.

Generally speaking, Shannon entropy is a measure of signal complexity based on data symbolization which quantifies the degree of structure in a histogram. Shannon entropy can be expressed as:

$$(1/\log N) \sum_i p_i \log p_i$$

where $p_i$ is binned probability (probability that a value is within the "i"th bin of a histogram) and N is the total number of bins. A form of Shannon entropy of a time series of data values can be determined as follows. The data undergo symbolization (e.g., by assigning a binary value to each of the data values or to each of a set of secondary values generated from one or more of the data values, and then determining symbols each consisting of a predetermined number "n" of the binary values concatenated together, where the first bit of each symbol corresponds to a distinctive time). The above-mentioned binary values can be assigned based upon whether each data value or secondary value (to which a binary value is to be assigned) exceeds a predetermined threshold. Then, a histogram is determined by assigning the symbols within a selected time interval to bins in accordance with the numerical value of each symbol. The Shannon entropy of this histogram is then determined. The Shannon entropy is a measure of the degree of organization of the symbol-sequence histogram; in effect, it is a measure of how randomly the time series behaves, given the chosen length and time scales of observation. For "random" data, Shannon entropy is at least approximately equal to 1; for nonrandom data, Shannon entropy is greater than 0 but less than 1 (see for example Finney C. E. A., Green J. B. Jr., and Daw C. S., "Symbolic time-series analysis of engine combustion measurements", SAE Paper No. 980624 (1998) and Tang X. Z., Tracy E. R., "Data compression and information retrieval via symbolization", Chaos 8, pp. 688-696 (1998)).

Generally speaking, Kolmogorov entropy is a measure of how chaotic a dynamic system is. Kolmogorov entropy is a measure of complexity of a signal that is indicative of a times series of data values, where the time series of data values is considered as a trajectory $x(t)=[x_1(t), \ldots, x_d(t)]$ of a dynamical system on a strange attractor (with a d-dimensional phase space partitioned into bins of size $l^d$), measured at intervals of time $\tau$. The Kolmogorov entropy, K, of such a times series can be expressed (in the limit as $\tau$ goes to 0, "l" goes to 0, and N goes to $\infty$) as:

$$K = (1/N\tau) \sum_{i0,\ldots iN} Pi0 \ldots iN \log Pi0 \ldots iN,$$

where $Pi0 \ldots iN$ is the joint probability that the trajectory is in bin $i_0$ at time t=0, in bin $i_1$ at time t=$\tau$, . . . , and in bin $i_N$ at time t=N$\tau$. Thus, in the case that the time series of data values is indicative of regular motion, K=0. In the case that the system displays deterministic chaos, K is in the range 0<K<1.

The Daw adaptation of the Delft maximum-likelihood estimator of Kolmogorov entropy (sometimes referred to as Kolmogorov-Sinai entropy) is a measure of signal complexity (see Schouten J. C., Takens F., van den Bleek C. M., "Maximum-likelihood estimation of the entropy of an attractor", Physical Review E 49, pp. 126-129 (1994) and Schouten J. C., van den Bleek C. M., "Monitoring the quality of fluidization using the short-term predictability of pressure fluctuations", AIChE Journal 44: 48-60 (1998), which are incorporated herein by reference). Briefly, the estimator ($K_{ML}$) quantifies the rate at which entropy is generated in the attractor by measuring the time for nearby trajectory segments to diverge. The method relies on a time-scale parameter, the segment length, and a length-scale parameter; the cutoff length. Based on these parameters, a single entropy value is obtained in accordance with some embodiments of the invention for each of a number of subsets of a time series of reaction parameter data values (measured during a time interval during a polymerization reaction in a fluidized bed reactor system), each of the subsets including reaction parameter data values in a different one of a sequence of sub-intervals (windows having predetermined duration) of the time interval. This number is compared over a range of bed operating conditions to correlate signal complexity with a sheeting propensity.

When Kolmogorov entropy is determined for subsets of reaction parameter data values measured during a time interval during a polymerization reaction in a fluidized bed reactor system, each of the subsets including reaction parameter data values in a different one of a sequence of sub-intervals (windows having predetermined duration) of the time interval, the inventors have recognized that a decrease over time of Kolmogorov entropy typically suggests a decrease in mixing in the fluidized bed reactor, a decrease in reactor continuity, and excess polymer formation on and/or near the reactor wall.

Figure 2:
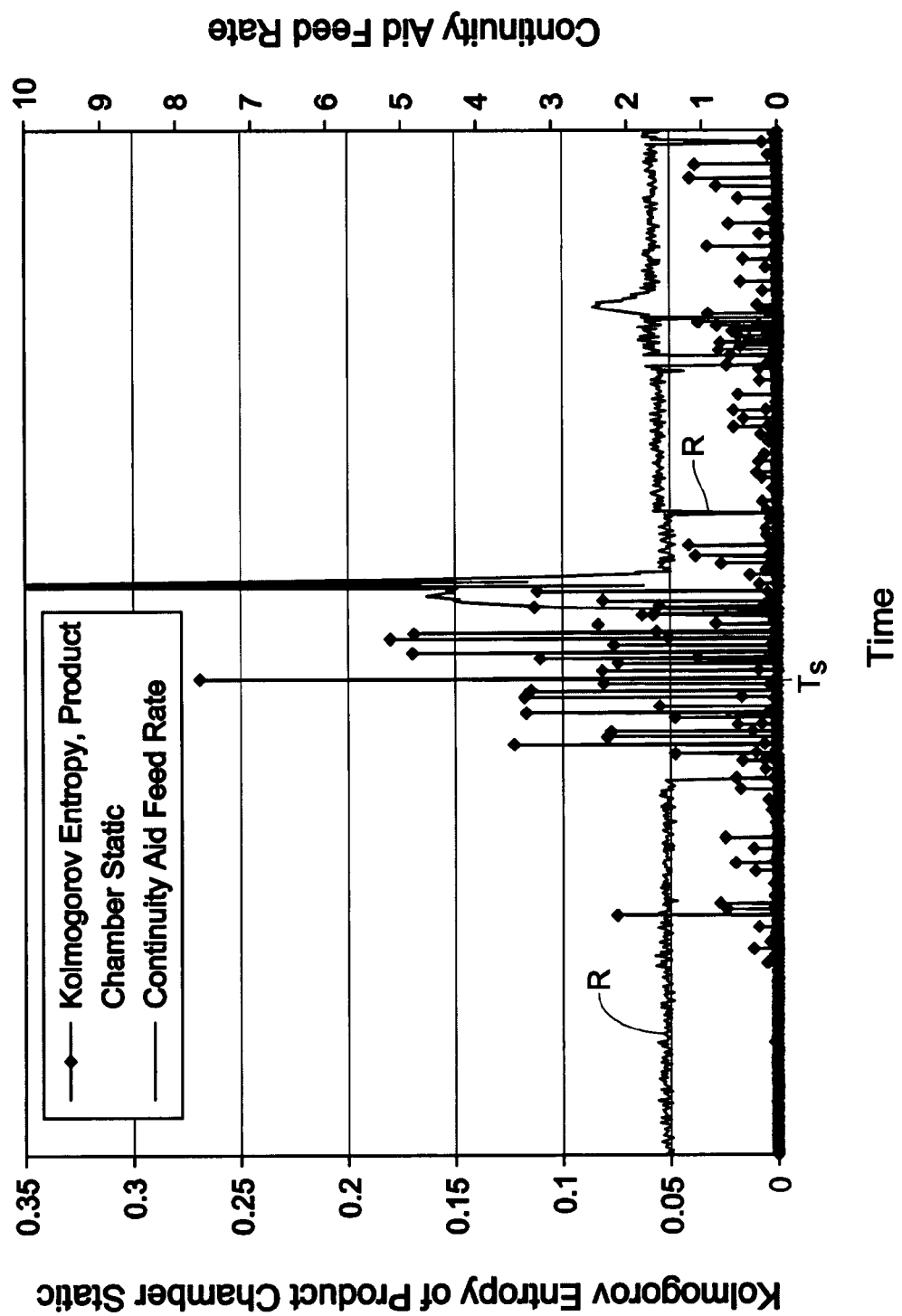
FIG. 2 is a graph of Kolmogorov entropy (computed in a sequence of time windows) of a time series of product chamber static data (indicative of measured charge on the product discharge vessel of a fluidized bed reactor system during a polymerization reaction) as a function of time (the center time of each window). Also, the flow rate of a continuity additive into the reactor as a function of time (curve "R") is shown.
Figure 3:
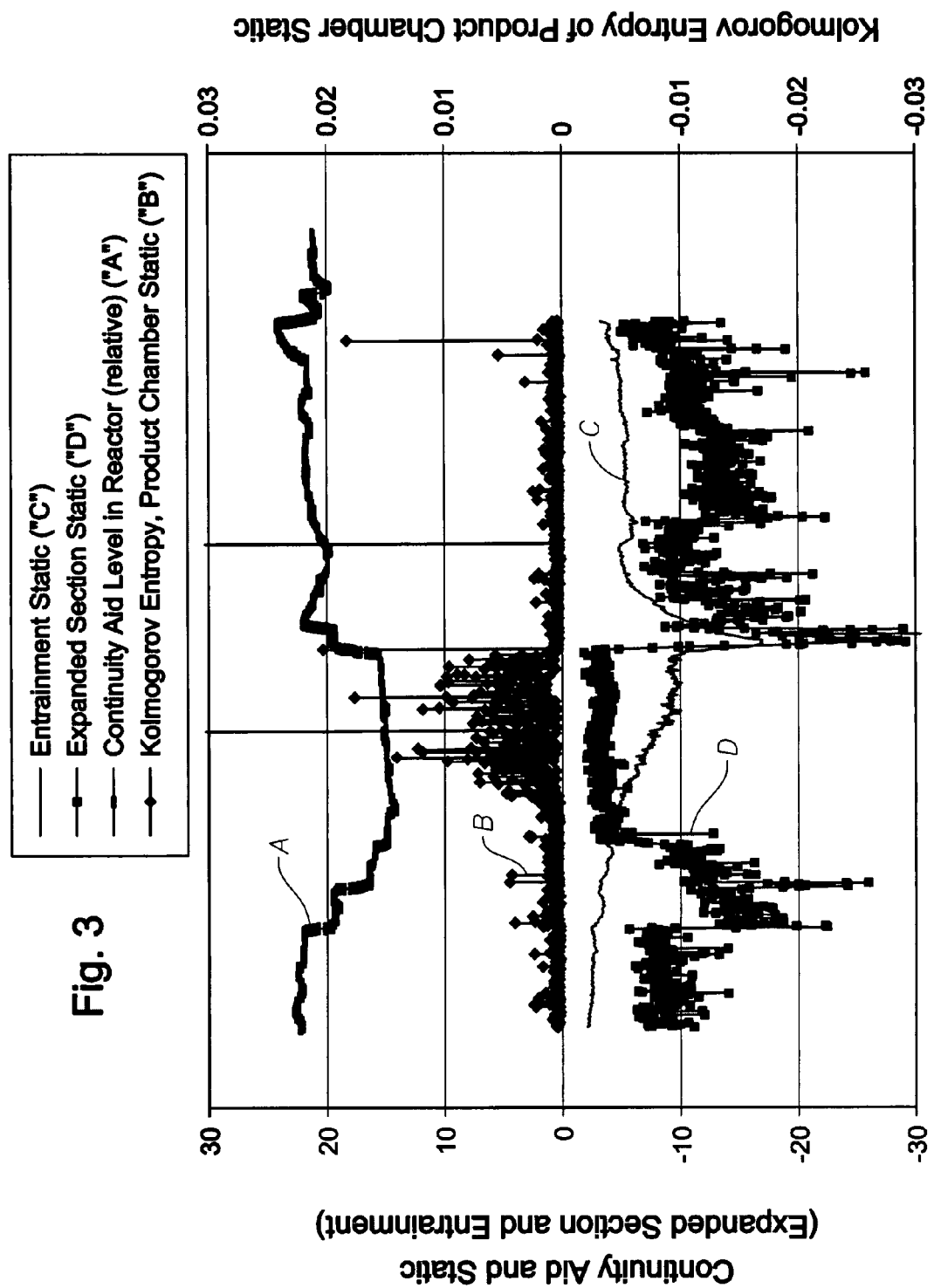
FIG. 3 is a set of two graphs. The upper graph plots Kolmogorov entropy (computed in a sequence of time windows) of a time series of product chamber, static data (indicative of measured charge on the product discharge vessel of a fluidized bed reactor system during a polymerization reaction) as a function of time (the center time of each window). This is curve "B." Also, the flow rate of a continuity additive into the reactor as a function of time (curve "A") is shown. The lower graph plots the mean value (computed in the same sequence of time windows) of a time series of entrainment static charge values (curve "C") measured during the same reaction using an entrainment static probe in the system's recycle line (e.g., recycle line 31 of FIG. 1) as a function of time (the center time of each window) and the mean value (computed in the same sequence of time windows) of a time series of static charge values (curve "D") measured during the same reaction using a static probe in the reactor's expanded section (e.g., expanded section 19 of FIG. 1) as a function of time (the center time of each window). The horizontal axes of both graphs indicate the same time interval.

With reference to FIGS. 2 and 3, we next describe a class of embodiments of the inventive method in which Kolmogorov entropy is determined for subsets (of reaction parameter data values) of a time series of reaction parameter data, each of the subsets including reaction parameter data values in a different time interval (window) of a sequence of time intervals during a polymerization reaction in a fluidized bed reactor system.

In FIG. 2, the Kolmogorov entropy values plotted versus time (over a three day time period in five minute increments) were generated from a time series of product chamber static charge values measured during a polyethylene-producing polymerization reaction in a fluidized bed reactor system using a product discharge chamber static sensor (of the same type as product discharge chamber static sensor 118 of FIG. 1) positioned to measure static charge transferred from resin product discharged from the reactor to the system's product discharge vessel (of the same type included in product discharge subsystem 20 of FIG. 1). Each plotted Kolmogorov entropy value was computed from a different sub-sequence of the static charge values in a different one of a sequence of time windows.

During operation of the reactor system, static charge accumulates on the product discharge vessel as polymer resin product is discharged from the fluidized bed reactor into the vessel. A product discharge chamber static sensor (e.g., sensor 118 of FIG. 1) can measure (in on-line fashion) static charge transferred to the product discharge vessel during each of a sequence of intervals. For example, static charge transferred to the product discharge vessel can be measured during each of a sequence of intervals while the vessel is filled, or (each time the product discharge vessel is emptied) the total amount of static charge transferred to the vessel since it was last emptied can be measured. The product chamber static data can be measured with the product discharge vessel functioning as a Faraday cup as the polymer product is discharged into it from the fluidized bed reactor. In a typical fluidized bed reactor system, the product discharge vessel (e.g., that of subsystem 20 of FIG. 1) has capacity to contain a large amount (e.g., 3000 lbs) of polymer product, and thus static charge indicative of a large amount of polymer product can be transferred to the product discharge vessel and measured to generate the product chamber static data.

During the reaction monitoring period in which the product chamber static charge values from which the entropy values of FIG. 2 were generated, a continuity additive (comprising "A" material in slurry) was fed into the reactor and its flow rate is shown as solid curve "R" (also labeled "Continuity Aid Feed Rate" in the box near the top of FIG. 2). As shown in FIG. 2 the flow of the continuity additive into the reactor was lost for a period of about 18 hours. During this period of loss of continuity additive flow, a resin sheeting incident occurred 13.75 hours after the loss of the continuity additive feed and corresponds to the peak in entropy values in FIG. 2. The inventors have recognized (consistent with inspection of the data plotted in FIG. 2) that the Kolmogorov entropy values of FIG. 2 were an excellent predictor of the resin sheeting event. Immediately after the loss of the continuity additive, the Kolmogorov entropy begins to increase (as shown in FIG. 2) several hours before the actual sheeting event. In addition, the sheeting event occurred at the same time (labeled time "$T_S$" in FIG. 2) that a maximum value in Kolmogorov entropy occurred. These data show that the Kolmogorov entropy of the product chamber static is an excellent predictor of an imminent sheeting event well in advance of the actual event.

More generally, the inventors have recognized that in typical cases, Kolmogorov entropy values generated in response to product chamber static data are reliably indicative of imminent sheeting (especially wall sheeting) in a polymerization reactor system. In contrast, measuring the static charge transferred (from polymer product and other substances within the reactor system) to a smaller element of the reactor system (e.g., a distributor plate or a static charge sensor in a gas recycle line) would generate static data that are indicative of charge of smaller amounts of polymer product than are product chamber static data, and Kolmogorov entropy values generated in response thereto would be less reliably indicative of imminent wall sheeting.

With reference to FIG. 3, we next describe another example of generation and use of Kolmogorov entropy values in accordance with an embodiment of the invention. The upper graph in FIG. 3 (labeled curve "A") is a plot of the feed rate of a continuity aid (above-defined material "A") as a solid mixture in the catalyst in amounts relative to a reference rate to allow the curve to be plotted on a scale similar to those of the other measured values of static. Lower values of curve "A" reflect lower feed rates of the continuity aid. In FIG. 3, curve "B" is a plot of the mean value of Kolmogorov entropy (computed in a sequence of time windows) of a time series of product chamber static data (indicative of measured charge on the product discharge vessel of a fluidized bed reactor system at a sequence of sample times during a measurement interval of a polyethylene-producing polymerization reaction) as a function of time (the center time of each window). The product chamber static data were generated using the same type of product discharge chamber static sensor used to generate the product chamber static data characterized by the entropy values plotted in FIG. 2. Each Kolmogorov entropy value in FIG. 3 was obtained from a different subset of the time series of product chamber static data values, each of the subsets including product chamber static data values in a different one of a sequence of sub-intervals (windows having predetermined duration) of the measurement interval.

Curve "C" of the lower graph in FIG. 3 is a plot of the mean value (computed in the same sequence of time windows as were the entropy values of curve "B" of the upper graph of FIG. 3) of a time series of entrainment static charge values measured during a time interval of the same reaction using an entrainment static probe in the system's recycle line (a sensor of the same type as sensor 111 in recycle line 31 of FIG. 1) as a function of time (the center time of each window). Each mean static charge value of curve C was obtained by averaging a different subset of the time series of entrainment static data values, each of the subsets including static data values in a different one of a sequence of sub-intervals (windows having predetermined duration) of the time interval.

Curve "D" of the lower graph in FIG. 3 plots the mean value (computed in the same sequence of time windows as were the mean static charge values of curve C) of a time series of static charge values measured during the same time interval of the same reaction using a static probe in the reactor's expanded section (a sensor of the same type as sensor 116 in reactor expanded section 19 of FIG. 1) as a function of time (the center time of each window). Each mean static charge value of curve D was obtained by averaging a different subset of the time series of static data values, each of the subsets including static data values in a different one of a sequence of windows (having predetermined duration) of the time interval.

During the reaction monitoring interval in which the static charge values from which the entropy and mean static charge values of FIG. 3 were generated, a resin sheeting incident occurred at a time corresponding to the steepest falling edges of curves C and D (these falling edges of curves C and D are aligned with each other). The inventors have recognized (consistent with inspection of the data plotted in FIG. 3) that the Kolmogorov entropy values of FIG. 3 were an excellent predictor of the resin sheeting event several hours before occurrence of the actual sheeting event. More specifically, the Kolmogorov entropy values varied rapidly with time prior to the sheeting event during a period (of roughly two-day duration) before the sheeting event (but had a relatively large average value during this period), and then dropped suddenly (to a much lower average value) at the onset of the sheeting event. In response to the sheeting event the relative feed rate of the continuity additive was increased (as shown by curve "A") to prevent reoccurrence of the sheeting.

In other tests, data from static, acoustic, temperature, and differential pressure sensors installed on a fluidized bed reactor system of the type shown in FIG. 1 were collected at sample rates of 100 Hz (during a polyethylene-producing polymerization reaction performed in the reactor system) and stored. During normal reactor operation (with no sheeting), each instrument produced a noisy signal characteristic of the random interaction of the well-mixed bed with each respective sensor. Undesired, non-uniformities in the bed caused subtle changes in the randomness of the sensor signals, typically manifested as spikes which occurred randomly with characteristic time scales of less than one second. Conventional Fourier-type power spectra (generated by Fourier-transforming time series of data values indicative of the sensor outputs) were found not to be reliably indicative of these random, asynchronous spikes because they were infrequent and phase-shifted. In contrast, Kolmogorov entropy values determined in accordance with some embodiments of the invention from the monitored reaction parameter data were found to be reliably indicative of these random, asynchronous spikes.

At least three known types of events have been found to be reliably determinable from Kolmogorov entropy values determined in accordance with embodiments of the invention: spiking caused by presence of sheets or the conditions leading to sheeting; entrainment spiking resulting when continuity additive clears up excess entrainment to reveal discharge events; and decreases in randomness resulting from a layer of fines on the reactor wall.

In some preferred embodiments, measured "high speed" reaction parameter data are processed in accordance with the invention (e.g., to generate a sequence of Kolmogorov entropy values). The expression "high speed" data is used herein to denote times series data values (indicative of a sequence of measured data samples) collected with a sample rate greater (and typically much greater) than 1 Hz. For example, in some embodiments at least one high speed skin thermocouple is used to generate time-domain reaction parameter data that are processed in accordance with the invention. A high speed thermocouple is configured to sense reactor temperature excursions of shorter duration than can a conventional thermocouple. A "high speed" (or "fast") thermocouple has sufficiently fast response to be sensitive to temperature spikes of duration on the order of a second (e.g., spikes having duration of one second or a few seconds) and is typically positioned not more than one half inch from the reactor wall.

As noted above, some embodiments of the inventive method include the steps of: (a) monitoring at least one reaction parameter of a polymerization reaction in a fluidized bed reactor system to generate (in on-line fashion) time-domain reaction parameter data; and (b) determining mathematical entropy (or an indicator of entropy or complexity) of each of at least two subsets of the reaction parameter data, each of the subsets including reaction parameter data values indicative of a different time interval of the reaction. As also noted above, the reaction parameter data generated in step (a) can be product chamber static data. Alternatively, the reaction parameter data generated in step (a) are static data other than product chamber static data. For example, the reaction parameter data can be or include one or more of bed static data indicative of static charge in the fluidized bed of a fluidized bed reactor (such static charge is sometimes referred to herein as reactor or "bed" static charge); carryover static data indicative of carryover static (e.g., entrainment static); and static charge measured using at least one static sensor in an expanded section of the reactor above the fluidized bed. In other embodiments, some or all of the reaction parameter data generated in step (a) are not indicative of static charge. For example, in some embodiments the reaction parameter data generated in step (a) are or include one or more of: acoustic or pressure (e.g., differential pressure) data; fluidized bulk density data generated from differential pressure data using appropriate sensors; and temperature data generated using at least one skin temperature sensor, wall temperature sensor, and/or other temperature sensor.

The carryover static data can be generated using at least one static probe positioned to monitor static charge outside the fluidized bed (i.e., in the entrainment zone). Typically, the reactor has a gas recycle line and the carryover static data are entrainment static data generated using at least one entrainment static probe positioned to monitor static charge in the gas recycle line. Static probes suitable for generating carryover static (e.g., entrainment static) data in some embodiments of the invention are described in above-referenced US Patent Application Publication No. 2005/0148742. Static probes suitable for generating carryover static data in some embodiments of the invention are static current probes; others are static voltage probes. Alternatively, the carryover static data are generated by other instruments (e.g., a Faraday cup to measure static charge of samples of entrained material collected from the recycle line with an isokinetic or other sampler).

In some embodiments in which bed static data are generated, the bed static data are generated using at least one static probe (e.g., a static probe of the type described in U.S. Pat. Nos. 4,532,311 5,648,581, 6,008,662 or another conventional reactor static probe) positioned to monitor static charge in the reactor at or near a portion of the reactor wall that bounds the fluidized bed.

Reaction monitoring in accordance with the invention can be used to identify when reaction conditions deviate from desirable operating conditions which are typically characterized by efficient, random mixing of particles in the reaction zone. Undesirable operating conditions are typically characterized by non-uniformities, including hot spots, cold bands caused by insulating layers of fines, and fused polymer sheets.

In preferred embodiments, relevant measured data from all reaction monitoring instruments and relevant calculated values are combined into an integrated computer display for presentation to users (e.g., plant operators). Such a computer display can be supplemented by process alarms or advisory notices to warn the users of conditions in the process that may be approaching those that will lead to sheeting (e.g., wall or dome sheeting) or other discontinuity events. The alarms or advisory notices can also be combined with recommended control actions to avoid the discontinuity event.

In some implementations of the above-mentioned embodiments, the inventive method also includes the step of controlling the reaction in response to entropy values (or other indicators of entropy or complexity) generated in step (b), typically in an effort to prevent (and preferably to prevent) the occurrence of sheeting or another discontinuity event and/or to maintain the reactor in a stable, non-sticking condition. For example, the control may be implemented by adjusting reaction temperature, or changing the superficial velocity of fluidizing gas, or controlling the feed rate of a continuity additive (e.g., aluminum distearate (material A) or ethoxylated amine (material B) additive, either neat or in oil slurry) into the reactor.

Figure 4:
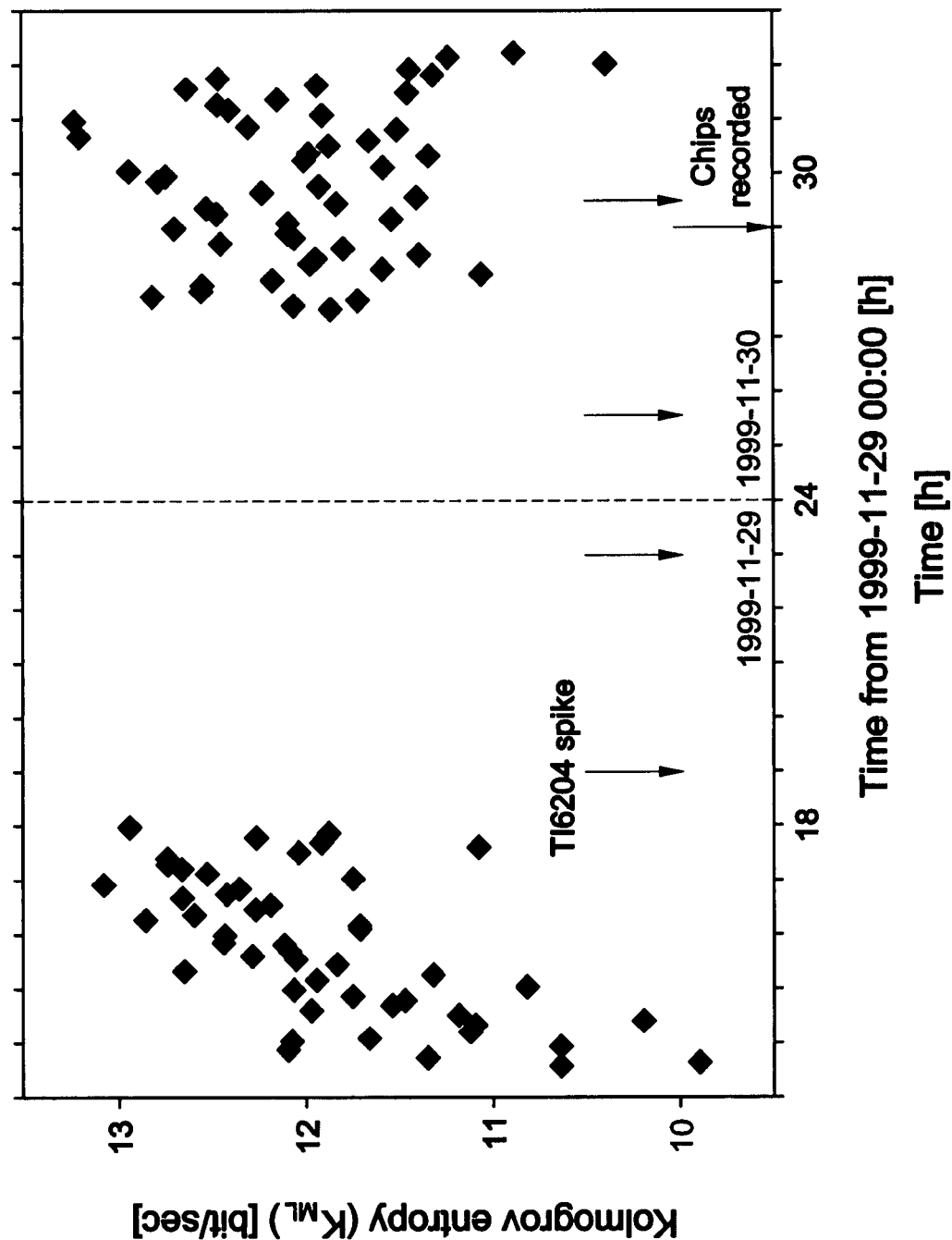
FIG. 4 is a plot of Kolmogorov entropy of subsets of a time series of fluidized bulk density data values generated while monitoring a polymerization reaction in a fluidized bed reactor. The entropy values are plotted versus time in units of hours after a specified initial time.

With reference to FIGS. 4 and 5, we next describe other examples of the inventive method.

FIG. 4 is a plot of Kolmogorov entropy of subsets of a time series of fluidized bulk density data (FBD) values generated while monitoring a polymerization reaction that produced very low density (VLDPE) polyethylene in a fluidized bed reactor. The entropy values ($K_{ML}$) are plotted versus time in units of hours after a specified initial time. FIG. 4 is described in the parent application. Several process changes occurred before time T=12:30 (i.e., about one half hour before the time indicated by the left end of the horizontal axis in FIG. 4). In the period between times T=13:23 and T=18:00, the FBD signal complexity as quantified by the Kolmogorov entropy steadily increased, as apparent from FIG. 4. Within an hour of the beginning of the data gap (which commences at about T=18:00 in FIG. 4), a bed temperature excursion was identified (this excursion is identified in FIG. 4 as a "TI6204 spike"). This data gap was the result of the sheeting event which caused pluggage of the pressure tap with subsequent loss of the signal until it was unplugged and reading resumed in the later portion of the time line plot of FIG. 4. Physical evidence of the sheeting event was provided by observance of chips and small sheets in the product discharge and purging section. Reactor operation subsequently recovered and normal operation took place as indicated by the drop in the Kolmogorov entropy in FIG. 4. The Kolmogorov entropy values are thus shown to be indicative of imminence of the bed temperature excursion.

FIG. 5 is a plot of Shannon entropy of subsets of a time series of temperature data values generated from the high-pass-filtered output of skin temperature sensors (of the same type as skin temperature sensors 8 of FIG. 1) monitoring a polyethylene-producing polymerization reaction in a fluidized bed reactor. The entropy values are plotted versus time in units of 5 second intervals. FIG. 5 is described in the parent application. The measured temperature data values were high-pass-filtered to eliminate the effects thereon of slow drift of reactor temperature, before the Shannon entropy values were determined from the filtered data. Each subset of the temperature data values comprised filtered temperature data values belonging to a different one of a sequence of sub-intervals of the monitoring period.

At about time T=5270 (along the horizontal axis of FIG. 5), a large sheeting event was observed in the reactor. The plotted symbolization-based Shannon entropy values exhibit a distinct decreasing trend leading up to the sheeting event, as apparent from FIG. 5. During a period of stable reactor operation (during approximately the time interval from T=500 to T=3000), Shannon entropy is relatively constant. At about the time T=3000, Shannon entropy unambiguously decreases, indicating a decrease in signal complexity. The inventors recognized that this decrease in complexity is a reliable indicator of decrease in mixing near the reactor wall and is thus a reliable predictor of sheeting.

We next describe examples of commercial-scale reactions (e.g., commercial-scale, gas-phase fluidized-bed polymerization reactions) that can be monitored and optionally also controlled in accordance with the invention. Some such reactions can occur in a reactor having the geometry of reactor 10 of FIG. 1. In different embodiments of the invention, performance of any of a variety of different reactors is monitored and optionally also controlled in accordance with the invention.

In some embodiments, a continuous gas phase fluidized bed reactor is monitored and optionally also controlled in accordance with the invention while it operates to perform polymerization as follows: The fluidized bed is made up of polymer granules. Gaseous feed streams of the primary monomer and hydrogen together with liquid or gaseous comonomer are mixed together in a mixing tee arrangement and introduced below the reactor bed into the recycle gas line. For example, the primary monomer is ethylene and the comonomer is 1-hexene. The individual flow rates of ethylene, hydrogen and comonomer are controlled to maintain fixed gas composition targets. The ethylene concentration is controlled to maintain a constant ethylene partial pressure. The hydrogen is controlled to maintain a constant hydrogen to ethylene mole ratio. The hexene is controlled to maintain a constant hexene to ethylene mole ratio (or alternatively, the flow rates of comonomer and ethylene are held at a fixed ratio). The concentration of all gases is measured by an on-line gas chromatograph to ensure relatively constant composition in the recycle gas stream. A solid or liquid catalyst is injected directly into the fluidized bed using purified nitrogen as a carrier. The feed rate of catalyst is adjusted to maintain a constant production rate. The reacting bed of growing polymer particles is maintained in a fluidized state by the continuous flow of make up feed and recycle gas through the reaction zone (i.e. the fluidized bed). In some implementations, a superficial gas velocity of 1 to 3 ft/sec is used to achieve this, and the reactor is operated at a total pressure of 300 psig. To maintain a constant reactor temperature, the temperature of the recycle gas is continuously adjusted up or down to accommodate any changes in the rate of heat generation due to the polymerization. The fluidized bed is maintained at a constant height by withdrawing a portion of the bed at a rate equal to the rate of formation of particulate product. The product is removed semi-continuously via a series of valves into a fixed volume chamber, which is simultaneously vented back to the reactor. This allows for highly efficient removal of the product, while at the same time recycling a large portion of the unreacted gases back to the reactor. This product is purged to remove entrained hydrocarbons and treated with a small steam of humidified nitrogen to deactivate any trace quantities of residual catalyst.

In other embodiments, a reactor is monitored and optionally also controlled in accordance with the invention while it operates to perform polymerization using any of a variety of different processes (e.g., slurry, or gas phase processes). For example, the reactor can be a fluidized bed reactor operating to produce polyolefin polymers by a gas phase polymerization process. This type of reactor and means for operating such a reactor are well known. In operation of such reactors to perform gas phase polymerization processes, the polymerization medium can be mechanically agitated or fluidized by the continuous flow of the gaseous monomer and diluent.

In some embodiments, a polymerization reaction that is a continuous gas phase process (e.g., a fluid bed process) is monitored and optionally also controlled in accordance with the invention. A fluidized bed reactor for performing such a process typically comprises a reaction zone and a so-called velocity reduction zone. The reaction zone comprises a bed of growing polymer particles, formed polymer particles and a minor amount of catalyst particles fluidized by the continuous flow of the gaseous monomer and diluent to remove heat of polymerization through the reaction zone. Optionally, some of the re-circulated gases may be cooled and compressed to form liquids that increase the heat removal capacity of the circulating gas stream when readmitted to the reaction zone. This method of operation is referred to as "condensed mode". A suitable rate of gas flow may be readily determined by simple experiment. Make up of gaseous monomer to the circulating gas stream is at a rate equal to the rate at which particulate polymer product and monomer associated therewith is withdrawn from the reactor and the composition of the gas passing through the reactor is adjusted to maintain an essentially steady state gaseous composition within the reaction zone. The gas leaving the reaction zone is passed to the velocity reduction zone where entrained particles are removed. Finer entrained particles and dust may be removed in a cyclone and/or fine filter. The gas is compressed in a compressor and passed through a heat exchanger wherein the heat of polymerization is removed, and then returned to the reaction zone.

The reactor temperature (Trx) of the fluid bed process is normally operated at the highest temperature that is feasible, given the stickiness or sintering characteristics of the polymer in the fluid bed. Although there is no generally recognized method for establishing the upper limit of reactor temperature, the upper limit is believed to be related to the sintering temperature of the polymer product.

In some embodiments, a reactor whose operation is monitored and optionally also controlled in accordance with the invention effects polymerization by a slurry polymerization process. A slurry polymerization process generally uses pressures in the range of from 1 to 50 atmospheres, and temperatures in the range of 0° C. to 120° C., and more particularly from 30° C. to 100° C. In a slurry polymerization, a suspension of solid, particulate polymer is formed in a liquid polymerization diluent medium to which monomer and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, a branched alkane in one embodiment. The medium employed should be liquid under the conditions of polymerization and relatively inert. When a propane medium is used the process must be operated above the reaction diluent critical temperature and pressure. In one embodiment, a hexane, isopentane or isobutane medium is employed.

In other embodiments, a reaction monitored and optionally also controlled in accordance with the invention is or includes particle form polymerization, or a slurry process in which the temperature is kept below the temperature at which the polymer goes into solution. In other embodiments, a reaction monitored and optionally also controlled in accordance with the invention is a loop reactor or one of a plurality of stirred reactors in series, parallel, or combinations thereof. Non-limiting examples of slurry processes include continuous loop or stirred tank processes.

A reaction monitored and optionally also controlled in accordance with some embodiments of the invention can produce homopolymers of olefins (e.g., homopolymers of ethylene), and/or copolymers, terpolymers, and the like, of olefins, particularly ethylene, and at least one other olefin. The olefins, for example, may contain from 2 to 16 carbon atoms in one embodiment; and in another embodiment, ethylene and a comonomer comprising from 3 to 12 carbon atoms in another embodiment; and ethylene and a comonomer comprising from 4 to 10 carbon atoms in yet another embodiment; and ethylene and a comonomer comprising from 4 to 8 carbon atoms in yet another embodiment. A reaction monitored and optionally also controlled in accordance with the invention can produce polyethylenes. Such polyethylenes can be homopolymers of ethylene and interpolymers of ethylene and at least one α-olefin wherein the ethylene content is at least about 50% by weight of the total monomers involved. Exemplary olefins that may be utilized in embodiments of the invention are ethylene, propylene, 1-butene, 1-pentene, 1-hexene, 1-heptene, 1-octene, 4-methylpent-1-ene, 1-decene, 1-dodecene, 1-hexadecene and the like. Also utilizable herein are polyenes such as 1,3-hexadiene, 1,4-hexadiene, cyclopentadiene, dicyclopentadiene, 4-vinylcyclohex-1-ene, 1,5-cyclooctadiene, 5-vinylidene-2-norbornene and 5-vinyl-2-norbornene, and olefins formed in situ in the polymerization medium. When olefins are formed in situ in the polymerization medium, the formation of polyolefins containing long chain branching may occur.

In the production of polyethylene or polypropylene, comonomers may be present in the polymerization reactor. When present, the comonomer may be present at any level with the ethylene or propylene monomer that will achieve the desired weight percent incorporation of the comonomer into the finished resin. In one embodiment of polyethylene production, the comonomer is present with ethylene in a mole ratio range in the gas phase of from 0.0001 (comonomer:ethylene) to 50, and from 0.0001 to 5 in another embodiment, and from 0.0005 to 1.0 in yet another embodiment, and from 0.001 to 0.5 in yet another embodiment. Expressed in absolute terms, in making polyethylene, the amount of ethylene present in the polymerization reactor may range to up to 1000 atmospheres pressure in one embodiment, and up to 500 atmospheres pressure in another embodiment, and up to 100 atmospheres pressure in yet another embodiment, and up to 50 atmospheres in yet another embodiment, and up to 10 atmospheres in yet another embodiment.

Hydrogen gas is often used in olefin polymerization to control the final properties of the polyolefin. For some types of catalyst systems, it is known that increasing concentrations (or partial pressures) of hydrogen increase the molecular weight or melt index (MI) of the polyolefin generated. The MI can thus be influenced by the hydrogen concentration. The amount of hydrogen in the polymerization can be expressed as a mole ratio relative to the total polymerizable monomer, for example, ethylene, or a blend of ethylene and hexane or propylene. The amount of hydrogen used in some polymerization processes is an amount necessary to achieve the desired MI (or molecular weight) of the final polyolefin resin. In one embodiment, the mole ratio in the gas phase of hydrogen to total monomer ($H_2$:monomer) is greater than 0.00001. The mole ratio is greater than 0.0005 in another embodiment, greater than 0.001 in yet another embodiment, less than 10 in yet another embodiment, less than 5 in yet another embodiment, less than 3 in yet another embodiment, and less than 0.10 in yet another embodiment, wherein a desirable range may comprise any combination of any upper mole ratio limit with any lower mole ratio limit described herein. Expressed another way, the amount of hydrogen in the reactor at any time may range to up to 10 ppm in one embodiment, or up to 100 or 3000 or 4000 or 5000 ppm in other embodiments, or between 10 ppm and 5000 ppm in yet another embodiment, or between 500 ppm and 2000 ppm in another embodiment.

A reactor monitored and optionally also controlled in accordance with some embodiments of the invention can be an element of a staged reactor employing two or more reactors in series, wherein one reactor may produce, for example, a high molecular weight component and another reactor may produce a low molecular weight component.

A reactor monitored and optionally also controlled in accordance with the invention can implement a slurry or gas phase process in the presence of a bulky ligand metallocene-type catalyst system and in the absence of, or essentially free of, any scavengers, such as triethylaluminum, trimethylaluminum, triisobutylaluminum and tri-n-hexylaluminum and diethyl aluminum chloride, dibutyl zinc and the like. By "essentially free", it is meant that these compounds are not deliberately added to the reactor or any reactor components, and if present, are present to less than 1 ppm in the reactor.

A reactor monitored and optionally also controlled in accordance with the invention can employ one or more catalysts combined with up to 10 wt % of a metal-fatty acid compound, such as, for example, an aluminum stearate, based upon the weight of the catalyst system (or its components). Other metals that may be suitable include other Group 2 and Group 5-13 metals. In other embodiments, a solution of the metal-fatty acid compound is fed into the reactor. In other embodiments, the metal-fatty acid compound is mixed with the catalyst and fed into the reactor separately. These agents may be mixed with the catalyst or may be fed into the reactor in a solution, a slurry, or as a solid (preferably as a powder) with or without the catalyst system or its components.

In a reactor monitored and optionally also controlled in accordance with some embodiments of the invention, supported catalyst(s) can be combined with activators and can be combined by tumbling and/or other suitable means, with up to 2.5 wt % (by weight of the catalyst composition) of an antistatic agent, such as an ethoxylated or methoxylated amine, an example of which is Kemamine AS-990 (ICI Specialties, Bloomington Del.). Other antistatic compositions include the Octastat family of compounds, more specifically Octastat 2000, 2500, 3000, and 5000.

Metal fatty acids and antistatic agents can be added as either solid slurries, solutions, or as solids (preferably as powders) as separate feeds into the reactor. One advantage of this method of addition is that it permits on-line adjustment of the level of the additive.

Examples of polymers that can be produced in accordance with the invention include the following: homopolymers and copolymers of C2-C18 alpha olefins; polyvinyl chlorides, ethylene propylene rubbers (EPRs); ethylene-propylene diene rubbers (EPDMs); polyisoprene; polystyrene; polybutadiene; polymers of butadiene copolymerized with styrene; polymers of butadiene copolymerized with isoprene; polymers of butadiene with acrylonitrile; polymers of isobutylene copolymerized with isoprene; ethylene butene rubbers and ethylene butene diene rubbers; and polychloroprene; norbornene homopolymers and copolymers with one or more C2-C18 alpha olefin; terpolymers of one or more C2-C18 alpha olefins with a diene.

Monomers that can be present in a reactor monitored and optionally also controlled in accordance with the invention include one or more of C2-C18 alpha olefins such as ethylene, propylene, and optionally at least one diene, for example, hexadiene, dicyclopentadiene, octadiene including methyloctadiene (e.g., 1-methyl-1,6-octadiene and 7-methyl-1,6-octadiene), norbornadiene, and ethylidene norbornene; and readily condensable monomers, for example, isoprene, styrene, butadiene, isobutylene, chloroprene, acrylonitrile, cyclic olefins such as norbornenes.

Fluidized bed polymerization can be monitored and optionally also controlled in accordance with some embodiments of the invention. The reaction can be any type of fluidized polymerization reaction and can be carried out in a single reactor or multiple reactors such as two or more reactors in series.

In various embodiments, any of many different types of polymerization catalysts can be used in a polymerization process monitored and optionally also controlled in accordance with the present invention. A single catalyst may be used, or a mixture of catalysts may be employed, if desired. The catalyst can be soluble or insoluble, supported or unsupported. It may be a prepolymer, spray dried with or without a filler, a liquid, or a solution, slurry/suspension or dispersion. These catalysts are used with cocatalysts and promoters well known in the art. Typically these are alkylaluminums, alkylaluminum halides, alkylaluminum hydrides, as well as aluminoxanes. For illustrative purposes only, examples of suitable catalysts include Ziegler-Natta catalysts, Chromium based catalysts, Vanadium based catalysts (e.g., vanadium oxychloride and vanadium acetylacetonate), Metallocene catalysts and other single-site or single-site-like catalysts, Cationic forms of metal halides (e.g., aluminum trihalides), anionic initiators (e.g., butyl lithiums), Cobalt catalysts and mixtures thereof, Nickel catalysts and mixtures thereof, rare earth metal catalysts (i.e., those containing a metal having an atomic number in the Periodic Table of 57 to 103), such as compounds of cerium, lanthanum, praseodymium, gadolinium and neodymium.

In various embodiments, a polymerization reaction monitored and optionally also controlled in accordance with the invention can employ other additives, such as (for example) inert particulate particles.

It should be understood that while some embodiments of the present invention are illustrated and described herein, the invention is not to be limited to the specific embodiments described and shown.

What is claimed is:

1. A method for monitoring a resin-producing polymerization reaction in a fluidized bed reactor system wherein the reactor system comprises a fluidized bed reactor and a product discharge vessel into which polymer product is discharged from the fluidized bed reactor, the method including the steps of:
(a) monitoring at least one reaction parameter of the reaction to generate in on-line fashion time-domain reaction parameter data, wherein the reaction parameter data includes static data and the monitoring includes measuring product chamber static data indicative of static charge transferred from the polymer product to the product discharge vessel during each of a sequence of intervals; and
(b) determining mathematical entropy of each of at least two subsets of the reaction parameter data, each of said subsets of the reaction parameter data including data values in a different one of a sequence of different time intervals.

2. The method of claim 1, wherein the mathematical entropy is Kolmogorov entropy.

3. The method of claim 2, also including the step of:
determining from entropy values generated in step (b) at least one indication of at least one of degree of resin stickiness, approach to or imminence of resin stickiness, likelihood of imminent resin stickiness, and an approach to or imminence of an unsafe or undesired reactor operating condition that can result in at least one of sheeting and chunking.

4. The method of claim 1, wherein the mathematical entropy is Shannon entropy.

5. The method of claim 4, also including the step of:
determining from entropy values generated in step (b) at least one indication of at least one of degree of resin stickiness, approach to or imminence of resin stickiness, likelihood of imminent resin stickiness, and an approach to or imminence of an unsafe or undesired reactor operating condition that can result in at least one of sheeting and chunking.

6. The method of claim 1, wherein the product chamber static data are indicative of static charge transferred to the product discharge vessel during each of a sequence of intervals while said product discharge vessel is filled.

7. The method of claim 1, wherein the product chamber static data comprise data values, each indicative of static charge transferred to the product discharge vessel since said vessel was last emptied.

8. The method of claim 1, wherein the product discharge vessel functions as a Faraday cup during measurement of the product chamber static data.

9. The method of claim 1, also including the step of determining from entropy values generated in step (b) at least one indication of imminent wall sheeting.

10. The method of claim 1, wherein the reaction parameter data generated in step (a) are carryover static data.

11. The method of claim 1, wherein the reaction parameter data generated in step (a) are entrainment static data.

12. The method of claim 1, wherein the reaction parameter data generated in step (a) are acoustic emission data.

13. The method of claim 1, wherein the reaction parameter data generated in step (a) are differential pressure data.

14. The method of claim 1, wherein the reaction parameter data generated in step (a) are high speed reaction parameter data.

15. The method of claim 14, wherein the high speed reaction parameter data are bed temperature data.

16. The method of claim 14, wherein the high speed reaction parameter data are skin temperature data.

17. The method of claim 1, also including the step of:
(c) determining from entropy values generated in step (b) at least one indication of at least one of degree of resin stickiness, approach to or imminence of resin stickiness, likelihood of imminent resin stickiness, and an approach to or imminence of an unsafe or undesired reactor operating condition that can result in at least one of sheeting and chunking.

18. The method of claim 17, wherein step (c) includes the step of generating a signal indicative of at least one of degree of resin stickiness, approach to or imminence of resin stickiness, likelihood of imminent resin stickiness, and an approach to or imminence of an unsafe or undesired reactor operating condition that can result in at least one of sheeting and chunking.

19. The method of claim 17, wherein step (c) includes the step of generating a display indicative of at least one of degree of resin stickiness, approach to or imminence of resin stickiness, likelihood of imminent resin stickiness, and an approach to or imminence of an unsafe or undesired reactor operating condition that can result in at least one of sheeting and chunking.

20. The method of claim 17, also including the step of:
(d) controlling the reaction in response to the at least one indication determined in step (c).

21. The method of claim 20, wherein step (d) includes the step of adjusting reaction temperature.

22. The method of claim 20, wherein step (d) includes the step of controlling a feed rate of a continuity additive.

23. The method of claim 20, wherein step (d) includes the step of controlling a feed rate of an induced condensing agent.

24. The method of claim 1, also including the step of controlling the reaction in response to at least one mathematical entropy value determined in step (b) in an effort to prevent occurrence of a discontinuity event.

25. The method of claim 1, wherein the reaction polymerizes ethylene and at least one comonomer in the presence of a catalyst selected from a group consisting of Ziegler-Natta, chromium, chromium oxide, $AlCl_3$, cobalt, iron, palladium, and metallocene catalyst.

26. The method of claim 1, wherein the reaction produces polyethylene.

27. The method of claim 1, wherein the reaction produces a polyolefin.

28. A method for monitoring a resin-producing polymerization reaction in a fluidized bed reactor system, including the steps of:
(a) monitoring at least one reaction parameter of the reaction to generate in on-line fashion time-domain reaction parameter data wherein the reaction parameter data includes static data;
(b) determining an indicator of at least one of entropy and complexity of each of at least two subsets of the reaction parameter data, each of said subsets of the reaction parameter data including data values in a different one of a sequence of different time intervals; and
(c) determining, from values of the indicator determined in step (b), at least one indication of at least one of degree of resin stickiness, approach to or imminence of resin stickiness, likelihood of imminent resin stickiness, and an approach to or imminence of an unsafe or undesired reactor operating condition that can result in at least one of sheeting and chunking.

29. The method of claim 28, wherein the indicator is Kolmogorov entropy.

30. The method of claim 28, wherein the indicator is Shannon entropy.

31. The method of claim 28, wherein the indicator is a Lyapunov exponent.

32. The method of claim 28, wherein the reactor system includes a fluidized bed reactor and a product discharge vessel into which polymer product is discharged from the fluidized bed reactor, and step (a) includes the step of:
measuring product chamber static data indicative of static charge transferred from the polymer product to the product discharge vessel during each of a sequence of intervals.

33. The method of claim 32, wherein the product chamber static data are indicative of static charge transferred to the product discharge vessel during each of a sequence of intervals while said product discharge vessel is filled.

34. The method of claim 32, wherein the product chamber static data comprise data values, each indicative of static charge transferred to the product discharge vessel since said vessel was last emptied.

35. The method of claim 32, wherein the product discharge vessel functions as a Faraday cup during measurement of the product chamber static data.

36. The method of claim 32, wherein step (c) includes the step of determining from the values of said indicator at least one indication of imminent wall sheeting.

37. The method of claim 28, wherein the reaction parameter data generated in step (a) are carryover static data.

38. The method of claim 28, wherein the reaction parameter data generated in step (a) are entrainment static data.

39. The method of claim 28, wherein the reaction parameter data generated in step (a) are acoustic emission data.

40. The method of claim 28, wherein the reaction parameter data generated in step (a) are differential pressure data.

41. The method of claim 28, wherein the reaction parameter data generated in step (a) are high speed reaction parameter data.

42. The method of claim 41, wherein the high speed reaction parameter data are skin temperature data.

43. The method of claim 28, wherein step (c) includes the step of generating a signal indicative of at least one of degree of resin stickiness, approach to or imminence of resin stickiness, likelihood of imminent resin stickiness, and an approach to or imminence of an unsafe or undesired reactor operating condition that can result in at least one of sheeting and chunking.

44. The method of claim 28, wherein step (c) includes the step of generating a display indicative of at least one of degree of resin stickiness, approach to or imminence of resin stickiness, likelihood of imminent resin stickiness, and an approach to or imminence of an unsafe or undesired reactor operating condition that can result in at least one of sheeting and chunking.

45. The method of claim 28, also including the step of:
(d) controlling the reaction in response to the at least one indication determined in step (c).

46. The method of claim 45, wherein step (d) includes the step of adjusting reaction temperature.

47. The method of claim 45, wherein step (d) includes the step of controlling a feed rate of a continuity additive.

48. The method of claim 45, wherein step (d) includes the step of controlling a feed rate of an induced condensing agent.

49. The method of claim 28, also including the step of controlling the reaction in response to at least one value of the indicator determined in step (b) in an effort to prevent occurrence of a discontinuity event.

50. The method of claim 28, wherein the reaction polymerizes ethylene and at least one comonomer in the presence of a catalyst selected from a group consisting of Ziegler-Natta, chromium, chromium oxide, $AlCl_3$, cobalt, iron, palladium, and metallocene catalyst.

51. The method of claim 28, wherein the reaction produces polyethylene.

52. The method of claim 28, wherein the reaction produces a polyolefin.

* * * * *